(12) United States Patent
Parekh et al.

(10) Patent No.: US 11,857,656 B1
(45) Date of Patent: Jan. 2, 2024

(54) SYSTEMS, METHODS, AND KITS FOR ALTERING THE COLOR OF THE HAIR

(71) Applicant: L'Oreal, Paris (FR)

(72) Inventors: Aakash Parekh, Edison, NJ (US);
Ronak Rughani, Edison, NJ (US);
Martin Asare, Springfield, NJ (US);
Sivaramakrishnan Muthukrishnan, Bridgewater, NJ (US); Zhengzheng Liao, Cranford, NJ (US); Yuri Lvov, Ruston, LA (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/841,290

(22) Filed: Jun. 15, 2022

(51) Int. Cl.
| *A61Q 5/10* | (2006.01) |
| *A61K 8/26* | (2006.01) |
| *A61K 8/35* | (2006.01) |
| *A61K 8/84* | (2006.01) |
| *A61K 8/49* | (2006.01) |

(52) U.S. Cl.
CPC ............ *A61K 8/26* (2013.01); *A61K 8/35* (2013.01); *A61K 8/492* (2013.01); *A61K 8/84* (2013.01); *A61Q 5/10* (2013.01); *A61K 2800/43* (2013.01); *A61K 2800/884* (2013.01)

(58) Field of Classification Search
CPC . A61K 8/26; A61K 8/35; A61K 8/492; A61K 8/84; A61K 2800/43; A61K 2800/884; A61Q 5/10
USPC .............................................. 8/405
See application file for complete search history.

(56) References Cited

U.S. PATENT DOCUMENTS

| 7,691,398 | B2 | 4/2010 | Arai et al. | |
|---|---|---|---|---|
| 8,507,056 | B2 | 8/2013 | Lvov et al. | |
| 10,166,175 | B1 * | 1/2019 | Lvov | ............... A61Q 5/10 |
| 10,398,635 | B1 | 9/2019 | Elsen-Wahrer et al. | |
| 10,799,439 | B2 | 10/2020 | Lvov et al. | |
| 2019/0060196 | A1 | 2/2019 | Elsen et al. | |
| 2020/0078278 | A1 * | 3/2020 | Lvov | ............... A61Q 5/065 |

FOREIGN PATENT DOCUMENTS

| FR | 2940095 A1 | 6/2010 |
|---|---|---|
| FR | 3015893 A1 | 7/2015 |
| KR | 10-1943523 B1 | 1/2019 |
| WO | 2005/117537 A2 | 12/2005 |

(Continued)

OTHER PUBLICATIONS

Abdullayev, et al., "Halloysite clay nanotubes as a ceramic "skeleton" for functional biopolymer composites with sustained drug release," Journal of Materials Chemistry B, DOI: 10.1039/c3tb20059k, downloaded by Brigham Young University on Apr. 26, 2013, published on Apr. 4, 2013, on http://pubs.rsc.org, pp. 2894-2903.

(Continued)

*Primary Examiner* — Eisa B Elhilo
(74) *Attorney, Agent, or Firm* — THE MARBURY LAW GROUP, PLLC

(57) ABSTRACT

The disclosure relates to systems for altering the color of the hair, comprising a pre-treatment composition comprising at least one amine-based compound and a dyeing composition comprising at least one microtube-dye composite. The disclosure also relates to methods of altering the color of the hair using the systems, as well as kits comprising the systems.

25 Claims, 10 Drawing Sheets

(56) References Cited

FOREIGN PATENT DOCUMENTS

| WO | 2006/052276 A2 | 5/2006 |
| WO | 2007/053647 A2 | 5/2007 |
| WO | 2013/150268 A2 | 10/2013 |
| WO | 2015/097308 A1 | 7/2015 |

OTHER PUBLICATIONS

"Coloration capillaire à l'argile 1.0 noir," (Semi-Permanent Colouring Hair Care with Clay), retrieved from the Internet: https://www.cattier-paris.com/fr/coloration-capillaire-a-l-argile-1-0-noir-tc10.html, [Apr. 12, 2021].

Cavallaro, et al., "Hydrophobically Modified Halloysite Nanotubes as Reverse Micelles for Water-in-Oil Emulsion," Langmuir, American Chemical Society, https://doi.org/10.1021/acs.langmuir.5b01181, Jun. 26, 2015, pp. A-G.

"Garnier Hair Color Color Styler Intense Wash-Out Color, Blue Burst," Garnier, retrieved from the Internet: https://www.amazon.com/Garnier-Color-Styler-Intense-Wash-Out/dp/B00NA2YJDO [Apr. 12, 2021].

Garnier, "Garnier Hair Color Express Retouch Gray Hair Concealer, Instant Gray Coverage, Brown, 1 Count," retrieved from Internet: https://www.amazon.com/Garnier-Express-Retouch-Concealer-Coverage/dp/B07KJZFW21, [Apr. 12, 2021].

French Search Report and Written Opinion for counterpart FR Application No. 2108206, dated Apr. 12, 2022.

Santos et al., "Evolution of Hair Treatment and Care: Prospects of Nanotube-Based Formulations," Nanomaterials, vol. 9, No. 6, 903, XP055912001, Jun. 21, 2019, pp. 3-13.

Panchal et al., "Self-assembly of clay nanotubes on hair surface for medical and cosmetic formulations," Nanoscale, vol. 10, No. 38, XP055912034, Aug. 17, 2018, pp. 18205-18216.

Copending U.S. Appl. No. 17/219,868, "Systems, Methods, and Kits for Altering the Color of the Hair," Inventor: Zhengzheng Liao, filed Mar. 31, 2021.

Non-Final Office Action for copending U.S. Appl. No. 17/219,868, dated Aug. 9, 2022.

French Search Report and Written Opinion for counterpart Application No. FR 2207700, dated Jun. 26, 2023 (no translation available).

\* cited by examiner

SYSTEMS, METHODS, AND KITS FOR ALTERING THE COLOR OF THE HAIR

TECHNICAL FIELD

The present disclosure relates to systems, methods, and kits for altering the color of the hair.

BACKGROUND

Consumers desire to use cosmetic compositions to enhance the appearance of keratinous substrates such as hair, e.g., by changing the color, style, and/or shape of the hair, and/or by imparting various properties to hair, such as shine and conditioning. Many of the known compositions and processes for enhancing the appearance of the hair involve chemical treatment of the hair. For example, the process of altering the color of hair can involve dyeing the hair by depositing an artificial color onto the hair which provides a different shade or color to the hair.

Traditional hair dyeing processes include permanent and semi-permanent or temporary hair dyeing. Permanent hair dyeing compositions uses oxidation dye precursors, which are also known as primary intermediates or couplers. These oxidation dye precursors are colorless or weakly colored compounds which, when combined with oxidizing products, give rise to colored complexes by a process of oxidative condensation. The permanent hair dye compositions also contain ammonia or other alkalizing agents which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. On the other hand, semi-permanent or temporary hair dyeing compositions typically use pigments, liposoluble dyes, natural dyes, or direct dyes chosen from acidic (anionic), basic (cationic), or neutral direct dyes which are deposited onto the hair fiber to impart color to the hair.

It is known that traditional hair coloring compositions have drawbacks, however. For example, oxidative hair dyeing processes typically cause damage to the hair such as breakage, dryness, roughness, and/or brittleness, and/or scalp or skin irritation due to the use of hydrogen peroxide and alkaline agents required to achieve the permanent coloration of the hair fibers.

Semi-permanent or temporary hair dye compositions may provide chromatic color to the hair, but the color may lack persistence due to the nature of the interactions that bind the direct dyes to the hair fiber and/or light-sensitivity. In addition, semi-permanent or temporary hair dye compositions may also cause skin and/or scalp irritation. Additionally, semi-permanent or temporary hair dyes typically are not able to provide the same vibrancy or diversity of shades as permanent hair dye compositions.

It was previously discovered that alumino-silicate microtubes could be used as a carrier for synthetic or natural dyes, for example as described in U.S. Pat. No. 10,799,439. However, although this microtube-dye composite can be used to provide color to hair in a manner that does not cause damage to the hair or skin and/or scalp irritation, the process may lead to unsatisfactory color deposition and hair coloring efficiency.

The present inventors have now surprisingly discovered methods for coloring hair using a microtube-dye composite which provides enhanced color deposition and more vibrant hair colors.

SUMMARY

It has been surprisingly and unexpectedly found that systems, methods, and kits for altering the color of the hair according to the disclosure can provide more vibrant color to the hair, and have the advantage of reduced damage to the hair relative to traditional hair coloring processes.

In various embodiments, the disclosure relates to systems for altering the color of the hair comprising (a) a pre-treatment composition comprising at least one amine-based compound and optionally at least one solvent, and (b) a dyeing composition comprising at least one microtube-dye composite and optionally at least one solvent. The pre-treatment composition may, in various embodiments, comprise a total amount of amine-based compound(s) ranging from about 0.001% to about 20% by weight, relative to the total weight of the pre-treatment composition. The dyeing composition may, in various embodiments, comprise a total amount of microtube-dye composite(s) ranging from about 0.01% to about 15% by weight, based on the weight of the dyeing composition. In various embodiments, the amine-based compounds may be chosen from non-surface active amine-based compounds, and the dye may be chosen from synthetic or natural direct dyes.

In certain embodiments, the amine-based compounds are chosen from non-surface active amine-based compounds having a molecular weight of less than about 10,000, for example less than about 7,700, less than about 5,000, or less than about 2,500, such as ranging from about 50 to about 10,000, from about 50 to about 8,000, from about 50 to about 6,000, from about 50 to about 4,000, from about 50 to about 3,000, from about 50 to about 2,000, from about 100 to about 10,000, from about 100 to about 7,500, from about 100 to about 5,000, or from about 100 to about 2,500.

In certain embodiments, the amine-based compounds are chosen from non-surface active amine-based compounds having at least one nitrogen in the main chain and/or at least one imine grouping HN=C, such as, for example, amino acids such as arginine and/or lysine, polyamino acids such as polyarginine, and synthetic or natural polyamines, such as, for example, polyalkyleneimines, such as branched or unbranched C2-C8 or C2-C5 polyalkyleneimines. In certain embodiments, polyethyleneimine may be chosen. For example, polyethyleneimine having a molecular weight ranging from about 100 to about 5,000, from about 100 to about 3,500, from about 100 to about 2,500, or from about 100 to about 2,000 may be chosen.

Preferably, the pre-treatment and/or dyeing compositions have an acidic pH, for example a pH of about 7 or less, such as less than about 6, or less than about 5, e.g. ranging from about 2 to about 7, from about 2 to about 6, from about 2 to about 5, or from about 2 to about 4.

In at least one embodiment, the disclosure relates to systems comprising (a) a pre-treatment composition comprising at least one non-surface active amine-based compound having a molecular weight ranging from about 50 to about 5,000, and (b) a dyeing composition comprising at least one halloysite-dye composite comprising at least one hair dyeing agent and at least one solvent, wherein the pre-treatment composition and/or the dyeing composition each have a pH ranging from about 2 to about 7, such as about 2 to about 6, about 2 to about 5, or about 2 to about 4.

The disclosure further relates to methods of treating hair, e.g. altering the color of hair, by applying systems according to the disclosure to the hair. In various embodiments, the methods comprise (a) applying to the hair a pre-treatment composition according to the disclosure, and (b) applying to the hair a dyeing composition comprising according to the disclosure. Optionally, steps (a) and (b) may be repeated one or more times, with the same or different pre-treatment and/or dyeing composition(s).

In various embodiments, the methods may further comprise allowing the pre-treatment and/or dyeing compositions to remain on the hair for an optional leave-in period, for example up to about 60 minutes such as about 2 minutes to about 50 minutes or about 3 minutes to about 40 minutes. In further embodiments, the methods may comprise a step of drying the hair after the step of applying the pre-treatment composition, e.g. after an optional leave-in period, but before the step of applying the dyeing composition, which may comprise air-drying the hair or drying the hair with a hair dryer or hood, optionally with heat. The drying step in various embodiments may comprise drying the hair after the step of applying the pre-treatment composition (optionally after a leave-in period) without rinsing or otherwise removing the pre-treatment composition from the hair before drying the hair.

Kits for altering the color of the hair comprising the systems according to the disclosure are also disclosed. In various embodiments, the kits comprise (a) a first container containing a pre-treatment composition according to the disclosure, and (b) a second container containing a dyeing composition according to the disclosure.

BRIEF DESCRIPTION OF THE FIGURES

FIGS. 4A-4B are graphs demonstrating change in ΔE (y-axis) of hair treated with systems and methods according to the disclosure comprising exemplary pre-treatment compositions according to the disclosure followed by exemplary dyeing compositions according to the disclosure, compared to the change in ΔE of hair treated with pre-treatment compositions having the same pH but including non-amine-based compounds, followed by exemplary dyeing compositions according to the disclosure. These graphs demonstrate that pre-treatment compositions having non-surface active amine-based compounds provide surprisingly improved color deposition compared to pre-treatment compositions with non-amine-based compounds, even when the pH of the pre-treatment compositions are the same and/or the molecular weights of the pre-treatment agents are similar.

DETAILED DESCRIPTION

Figure 1A:
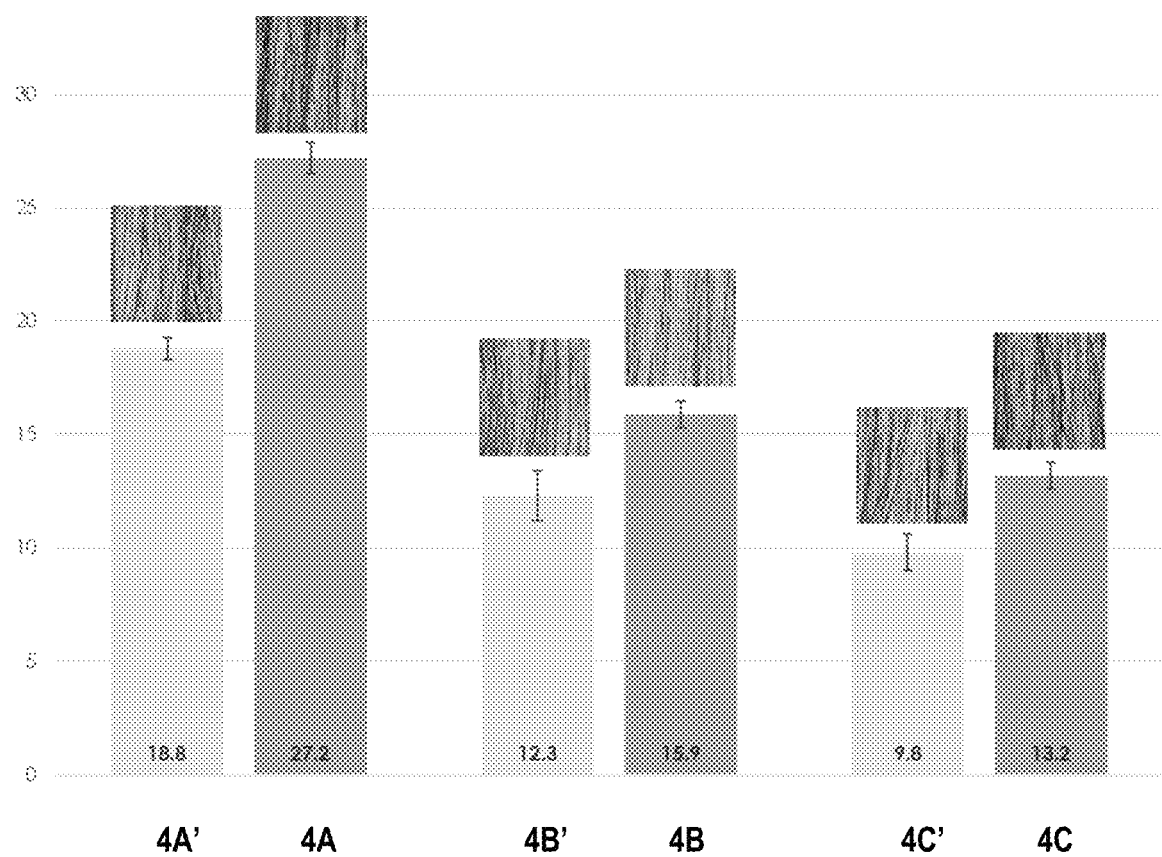
FIGS. 1A-1D are graphs demonstrating change in ΔE (y-axis) of hair treated with exemplary systems and methods according to the disclosure with pre-treatment compositions comprising non-surface active amine-based compounds followed by dyeing compositions comprising microtube-dye composites (4A-4J), compared to hair treated with comparative compositions and methods with no pre-treatment (4A'-4G'), demonstrating that systems and methods including pre-treatment compositions according to the disclosure have surprisingly improved color deposition.
Figure 1B:
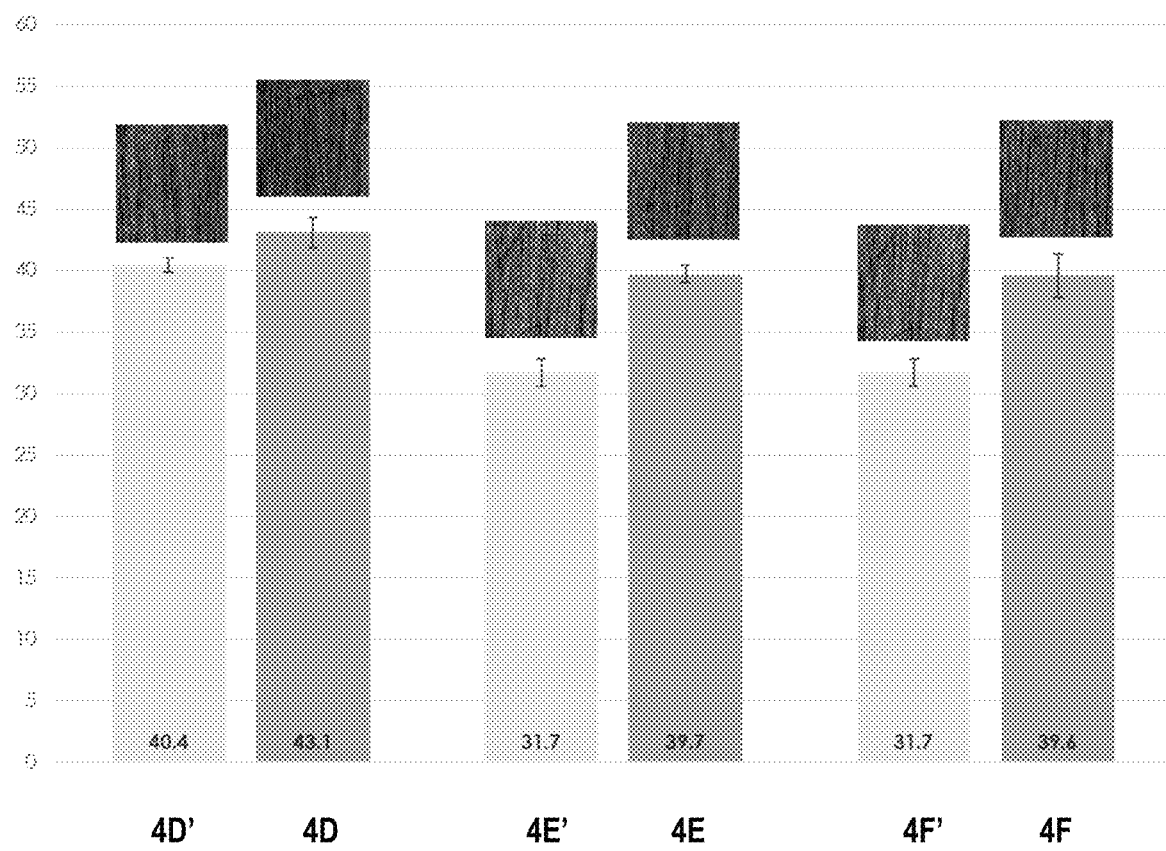
Figure 1C:
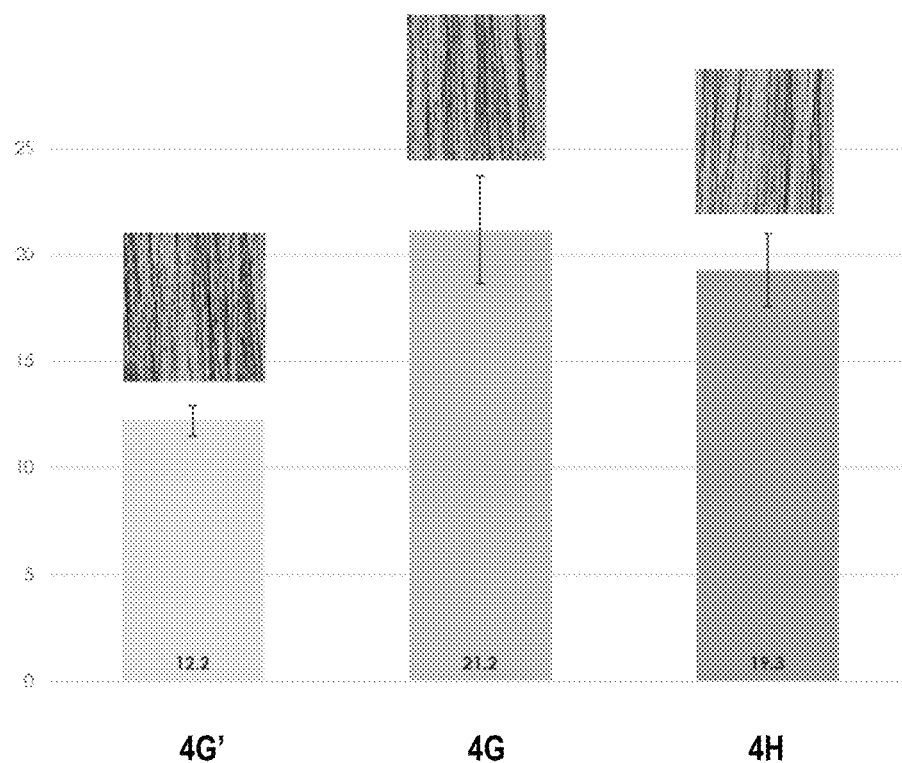
Figure 1D:
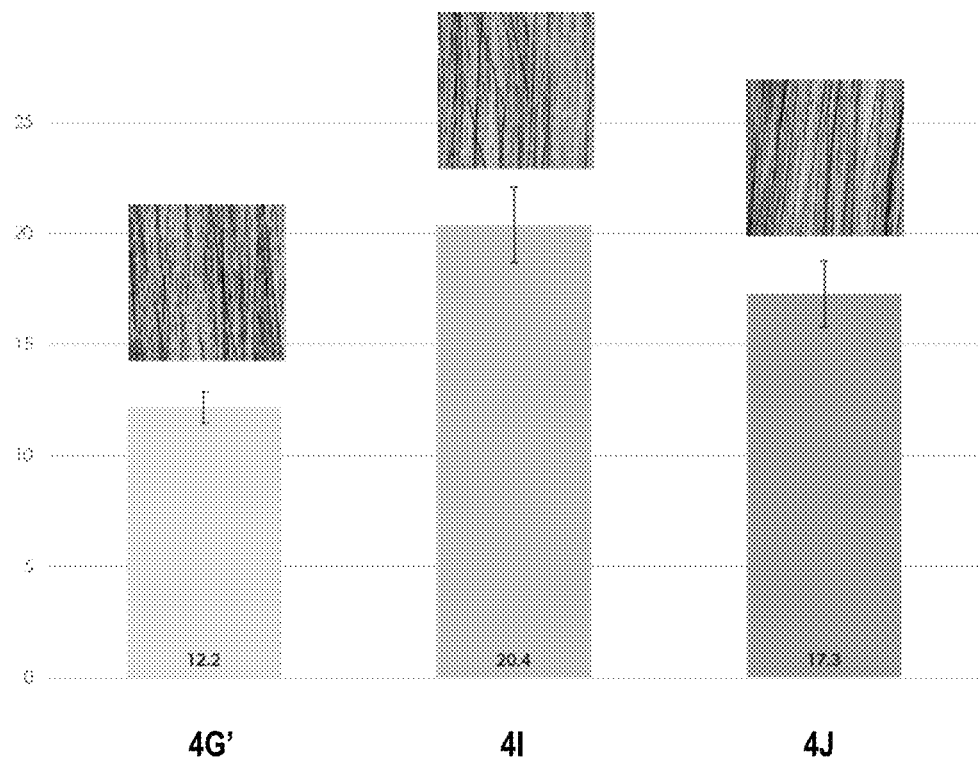

The disclosure relates to systems, methods, and kits for altering the color of the hair. The systems, methods, and kits according to the disclosure surprisingly and unexpectedly provide improved color deposition to the hair that results in more vibrant and satisfying coloration to the hair.

Systems

It has been surprisingly and unexpectedly discovered that when hair is treated with a system comprising a pre-treatment composition comprising at least one amine-based compound, and a dyeing composition comprising a microtube-dye composite, improved color deposition onto the hair and more vibrant hair color can be achieved.

Pre-Treatment Compositions

The systems according to the disclosure comprise at least one pre-treatment composition comprising at least one non-surface active amine-based compound, and optionally at least one solvent.

The non-surface active amine-based compounds useful in the pre-treatment compositions according to the disclosure have a molecular weight of less than about 10,000, such as less than about 8,000, less than about 6,000, less than about 5,000, less than about 4,000, less than about 3,000, or less than about 2,500. For example, the non-surface active amine-based compounds may, in various embodiments, have a molecular weight ranging from about 50 to about 10,000, from about 50 to about 9,000, from about 50 to about 8,000, from about 50 to about 7,000, from about 50 to about 6,000, from about 50 to about 5,000, from about 50 to about 4,000, from about 50 to about 3,000, from about 50 to about 2,000, from about 100 to about 10,000, from about 100 to about 9,000, from about 100 to about 8,000, from about 100 to about 7,000, from about 100 to about 6,000, from about 100 to about 5,000, from about 100 to about 4,000, from about 100 to about 3,000, or from about 100 to about 2,000. In some embodiments, the non-surface active amine-based compounds may have a molecular weight ranging from about 50 to about 7,500, from about 50 to about 2,500, from about 50 to about 1,500, from about 100 to about 7,500, from about 100 to about 2,500, or from about 100 to about 1,500.

In various embodiments, useful non-surface active amine-based compounds have one or more nitrogen atoms in the main chain or backbone of the compound, i.e. at least one nitrogen atom other than as part of a side chain attached to the main chain or backbone of the compound. It should be understood that such compounds may include nitrogen atom(s) in one or more side chains, but that such compounds will also include one or more nitrogen atoms in the main chain or backbone of the compound. For example, amino acids such as arginine and/or lysine may be used. In some embodiments, the non-surface active amine-based compound may comprise, consist essentially of, or consist of arginine.

In other embodiments, useful non-surface active amine-based compounds contain one or more imine groupings HN=C. For example, synthetic or natural polyamines may be chosen. In various embodiments polyalkyleneimines, such as branched or unbranched C2-C8 or C2-C5 polyalkyleneimines, may be chosen. For example, the amine-based compounds may be chosen from polyethyleneimine, polypropyleneimine, poly(allylamine), and/or polyvinylamine. In at least one embodiment, the amine-based compound comprises polyethyleneimine. As useful polyethyleneimines, mention may be made of the products available from BASF under the names LUPASOL or POLYIMIN, e.g. Lupasol® PS, Lupasol® PL, Lupasol® PR8515, Lupasol® G20, or Lupasol® G35. Optionally, dendrimers and derivatives of such polyalkyleneimines may also be used. In some embodiments, the non-surface active amine-based compound may comprise, consist essentially of, or consist of polyethyleneimine.

In other embodiments, polyamino acids may be chosen, such as, for example polyarginine.

Optionally, pre-treatment compositions according to the disclosure may comprise more than one non-surface active amine-based compound. In embodiments where more than one non-surface active amine-based compound is present, preferably at least one has a molecular weight of less than about 10,000, such as less than about 8,000, less than about 6,000, less than about 5,000, less than about 3,000, or less than about 2,500.

The total amount of non-surface active amine-based compounds may range from about 0.001% to about 25% by weight, relative to the total weight of the pre-treatment composition. For example, in some embodiments, the total amount of amine-based compounds may range from about 0.001% to about 20%, such as about 0.001% to about 15%, about 0.001% to about 10%, 0.001% to about 9%, about 0.001% to about 8%, about 0.001% to about 7%, about 0.001% to about 6%, about 0.001% to about 5%, about 0.001% to about 4%, about 0.001% to about 3%, about 0.001% to about 2.5%, about 0.001% to about 2%, about 0.001% to about 1.5%, about 0.001% to about 1%, about 0.001% to about 0.5%, about 0.01% to about 25%, about 0.01% to about 20%, about 0.01% to about 15%, about 0.01% to about 10%, 0.01% to about 9%, about 0.01% to about 8%, about 0.01% to about 7%, about 0.01% to about 6%, about 0.01% to about 5%, about 0.01% to about 4%, about 0.01% to about 3%, about 0.01% to about 2.5%, about 0.01% to about 2%, about 0.01% to about 1.5%, about 0.01% to about 1%, about 0.01% to about 0.5%, about 0.1% to about 25%, about 0.1% to about 20%, about 0.1% to about 15%, about 0.1% to about 10%, 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2.5%, about 0.1% to about 2%, about 0.1% to about 1.5%, about 0.1% to about 1%, or about 0.1% to about 0.5% by weight, relative to the total weight of the pre-treatment composition. In other embodiments, the total amount of non-surface active amine-based compounds ranges from about 0.2% to about 25%, about 0.2% to about 20%, about 0.2% to about 15%, about 0.2% to about 10%, about 0.2% to about 9%, about 0.2% to about 8%, about 0.2% to about 7%, about 0.2% to about 6%, about 0.2% to about 5%, about 0.2% to about 4%, about 0.2% to about 3%, about 0.2% to about 2.5%, about 0.2% to about 2%, about 0.2% to about 1.5%, about 0.2% to about 1%, about 0.5% to about 25%, about 0.5% to about 20%, about 0.5% to about 15%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2.5%, about 0.5% to about 2%, about 0.5% to about 1.5%, or about 0.5% to about 1% by weight, relative to the total weight of the pre-treatment composition.

The pre-treatment composition comprises at least one solvent, for example water, non-aqueous solvents, or a mixture thereof. In various embodiments, the solvent of the pre-treatment composition comprises, consists essentially of, or consists of water.

Exemplary non-aqueous solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, and mixtures thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. The organic solvents can be volatile or non-volatile compounds.

In certain embodiments, the pre-treatment composition comprises from about 60% to about 99.999% of a solvent, such as water, by weight. In certain embodiments, the pre-treatment composition comprises from about 75% to about 99.999% solvent by weight, such as from about 75% to about 99.99%, about 75% to about 99.9%, about 75% to about 99%, about 75% to about 98%, about 75% to about 97%, about 90% to about 99.9%, about 90% to about 99%, about 90% to about 98%, about 90% to about 97%, about 95% to about 99.9%, about 95% to about 99%, about 95% to about 98%, or about 95% to about 97%, by weight of the pre-treatment composition.

In various embodiments the systems comprise more than one pre-treatment composition, such as, for example, two or more pre-treatment compositions. In such embodiments, the non-surface active amine-based compound(s) present in the two or more pre-treatment compositions may be the same or different. Optionally, in such embodiments, at least one non-surface active amine-based compound has a molecular weight of less than about 10,000, such as less than about 8,000, less than about 6,000, less than about 5,000, less than about 3,000, or less than about 2,500.

The pre-treatment composition(s) may comprise additional components. By way of example only, the pre-treatment composition may comprise pH adjusters, preservatives, humectants, oils, fragrances, etc.

In various embodiments, the pre-treatment composition(s) have a pH of less than or equal to about 7, such as less than or equal to about 6, less than or equal to about 5, less than or equal to about 4, or less than or equal to about 3. For example, the pre-treatment composition may have a pH ranging from about 1 to about 7, such as from about 2 to about 6, from about 2.5 to about 5, or from about 3 to about 4.

It has been discovered that pre-treatment compositions having a lower pH and/or comprising amine-based compounds with a lower molecular weight may provide surprising color-enhancement efficacy. Therefore, in certain embodiments, it may be preferable for the pre-treatment composition(s) to comprise at least one non-surface active amine-based compound with a molecular weight of less than about 10,000, such as less than about 8,000, less than about 6,000, less than about 5,000, less than about 3,000, or less than about 2,500, for example ranging from about 100 to about 10,000, from about 100 to about 7,500, from about 100 to about 5,000, or from about 100 to about 2,500, and for the pre-treatment composition to have a pH of less than or equal to 7, such as ranging from about 1 to about 5 or from about 2 to about 4. In other embodiments, it may be preferable for the pre-treatment composition to comprise at least one non-surface active amine-based compound with a molecular weight of less than about 10,000 or less than about 5,000, for example ranging from about 100 to about 5,000 or about 100 to about 2,500, and for the pre-treatment composition to have a pH of less than or equal to 7, such as ranging from about 1 to about 5 or from about 2 to about 4.

Dyeing Composition

The systems according to the disclosure comprise at least one dyeing composition comprising at least one microtube-dye composite, and optionally at least one solvent. The dye of the composite may include at least one anionic, cationic, nonionic, or natural direct dye, as well as mixtures thereof.

The term "microtube" as used herein includes any tubular material having micron level dimensions or less (e.g., the length dimension of the tube being under about 1 mm), including nanotubes, or may refer to tubular structures having an outer diameter that is sub-micron and lengths under about 100 microns, such as under about 50 microns, or under about 10 microns. Various exemplary embodiments employ microtubes which are aluminosilicate in nature, such as halloysite and imogolite, or which are not aluminosilicate in nature, such as sepiolite or cylindrite.

Exemplary and non-limiting microtubes include, for example halloysite ($Al_2Si_2O_5(OH)_4$) microtubes. Halloysite forms as small cylinders (nanotubes) that may, for example, have a wall thickness ranging from about 10 to about 15 atomic aluminosilicate sheets, an outer diameter ranging from about 50 to about 60 nm, an inner diameter ranging from about 12 to about 20 nm, and a length ranging from about 0.5 to about 10 μm, with an average length of about 1 μm. Their outer surface is mostly composed of —Si—O—Si— and the inner surface of —Al—OH, and hence those surfaces are oppositely charged at approximately neutral pH. In various embodiments of the disclosure, the microtubes comprise, consist essentially of, or consist of halloysite.

The microtubes may be "loaded" with a hair dyeing agent, meaning that the dye agent is incorporated into the lumen of the microtube, in order to form the microtube-dye composite. The microtube-dye composite may be formed by methods known for loading microtubes (such as halloysite), for example as described in U.S. Pat. Nos. 8,507,056 and 10,799,439, and Abdullayev E. and Lvov Y., "Halloysite clay nanotubes as a ceramic 'skeleton' for functional biopolymer composites with sustained drug release," *J. Mater. Chem. B*, 1(23):2894-2903 (2013), all of which are incorporated herein by reference.

By way of example, a hair dyeing agent may be dissolved in an appropriate solvent, such as water, a non-aqueous solvent, or a mixture thereof, to form a solution. The amount of dye may be chosen such that it is near or at the solubility limit of the dye in the solvent. In one exemplary embodiment, the solution may contain from about 1% to about 20%, such as from about 1% to about 15%, by weight, of the hair dyeing agent. In another embodiment, the solution may contain from about 1 to about 20 mg of dye per mL solvent, such as from about 1 to about 15 mg of dye per mL of solvent. An appropriate amount of the microtube component may be added to the dye solution, for example in powder form, to form a dispersion. The amount of the microtube component may, for example, be chosen to provide a weight ratio of dye:microtube ranging from about 1:1 to about 5:1, such as from about 1:1 to about 4:1, from about 1:1 to about 3:1, or from about 1.5:1 to about 2.5:1, such as about 2:1, which may enhance color.

The dispersion may optionally be homogenized, sonicated, stirred, placed under vacuum, washed, and/or dried to provide microtubes loaded with the hair dyeing agent. For example, the dispersion may be sonicated for a period of time such as about 2-10 minutes, for example about 5 minutes, then mixed for a period of time such as about 10-60 minutes, for example about 30 minutes. The sonication and/or mixing steps can be repeated one or more times, and may be carried out under either ambient conditions, under vacuum and/or elevated temperature, or combinations thereof, until the microtubes are loaded with dye. Once the microtubes are loaded, the supernatant may be removed, e.g. by centrifuging, and the microtube-dye composite can be dried, for example in an oven at a temperature of at least 40° C., such as at least 45° C., for example about 50° C.

In one embodiment, the solvent may comprise, consist essentially of, or consist of water. For example, the solvent may be water and may include a component for aiding dissolution of the dye chosen, for example sodium carbonate.

In further embodiments, the solvent may comprise, consist essentially of, or consist of a non-aqueous solvent. Exemplary and non-limiting non-aqueous solvents that can be used for loading the hair dyeing agent into the microtubes include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n- propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbitan, acetine, diacetine, triacetine, sulfolane, acetone, and mixtures thereof.

In certain embodiments, the solvent may comprise both water and a non-aqueous solvent, for example from about 1% to about 99% water mixed with about 1% to about 99% non-aqueous solvent. It is within the ability of those skilled in the art to choose the appropriate solvent and/or combination of solvents, and amounts thereof, in order to dissolve the hair dyeing agents useful according to the disclosure.

In various embodiments, the internal and/or external surface of the microtube may be modified prior to loading with the hair dyeing agent, which may aid dye loading and/or the hair dyeing process. By way of example, the microtubes may be modified, e.g. with a surfactant such as sodium dodecyl sulphate, or may be made hydrophobic, which may be preferred when loading a hydrophobic dye. In one embodiment, the microtubes may be dispersed in a solution of anionic surfactant (e.g. at a weight ratio of about 1:1), optionally stirred and/or centrifuged, and optionally washed and/or dried, in order to produce microtubes modified with the anionic surfactant, having an increased net negative charge relative to unmodified microtubes.

In another embodiment, the microtubes may be made hydrophobic, for example by coupling a silane coupling agent to hydroxyl groups present at the surface of the microtubes to increase the contact angle of the microtube, or by absorption of anionic amphiphile molecules into the positive lumen. In various embodiments, the contact angle may be increased to at least about 30°, such as at least about 50°, at least about 75°, at least about 100°, at least about 115°, such as about 120°. Exemplary and non-limiting silane coupling agents include (3-glycidyloxypropyl) trimethoxy silane (GTMS), 3-aminopropyltriethoxy silane (APTES), hexamethyldisilazane (HMDS), and octadecyltrimethoxy silane (ODTMS). By way of example, the microtubes may be sonicated with the silane coupling agent in a solvent, e.g. water, an organic solvent, or a mixture thereof, followed by refluxing at increased temperature, e.g. greater than about 50° C. or greater than about 75° C., such as about 85° C.

In yet a further embodiment, the surface of the microtube may be selectively etched. For example, the inner surface of the halloysite lumen may be etched by treatment with acid, such as sulfuric acid, which may increase the diameter of the lumen. In one embodiment, the halloysite can be stirred in sulfuric acid (e.g. 1 M) at elevated temperature, e.g. greater than about 50° C. or greater than about 75° C., such as about 80° C., for a period of time such as at least 2 hours, at least 4 hours, at least 6 hours, or at least 8 hours. Such treatment can increase the loading capacity of the microtubes by 2, 3, 4, or even more times the pre-etching loading capacity.

Useful hair dyeing agents according to the disclosure included direct dyes such as anionic, cationic, nonionic, and natural hair dyeing agents, as well as mixtures of any two or more thereof. In certain embodiments, the hair dyeing agents comprise, consist essentially of, or consist of natural hair dyeing agents. In various embodiments, the compositions are free or essentially free of oxidative hair dyeing agents.

The term "anionic hair dyeing agent" is intended to mean any hair dyeing agent comprising in its structure at least one $CO_2R$ or $SO_3R$ substituent with R denoting a hydrogen atom or a cation originating from a metal or an amine, or an ammonium ion. By way of example, anionic hair dyeing agents may be chosen from acidic nitro direct dyes, acidic azo dyes, acidic azine dyes, acidic triarylmethane dyes, acidic indoamine dyes, acidic anthraquinone dyes, indigoid dyes, acidic natural dyes, and combinations thereof.

In one exemplary embodiment, the anionic hair dyeing agent may be chosen from the diaryl anionic azo dyes of formula (II) or (III):

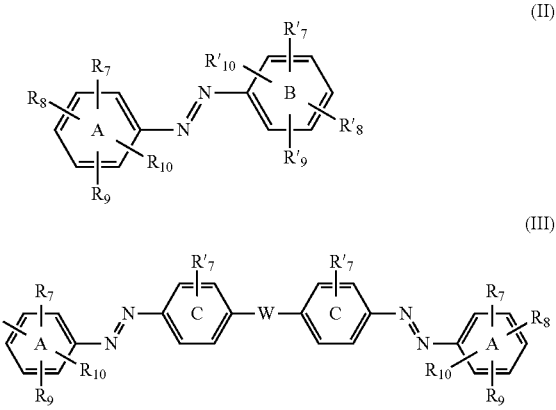

wherein:
$R_7$, $R_8$, $R_9$, $R_{10}$, $R'_7$, $R'_8$, $R'_9$ and $R'_{10}$, which may be identical or different, represent a hydrogen atom or a group chosen from:
alkyl;
alkoxy, alkylthio;
hydroxyl, mercapto;
nitro, nitroso;
$R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $M^+$ with $M^+$ representing a hydrogen atom or a cationic counterion;
$(O)CO^-$—, $M^+$ with $M^+$ as defined previously;
R"—$S(O)_2$—, with R" representing a hydrogen atom or an alkyl, aryl, (di)(alkyl)amino or aryl(alkyl)amino group; preferentially a phenylamino or phenyl group;
R'"—$S(O)_2$—X'— with R'" representing an alkyl or optionally substituted aryl group, X' as defined previously;
(di)(alkyl)amino;
aryl(alkyl)amino optionally substituted with one or more groups chosen from i) nitro; ii) nitroso; iii) $(O)_2S(O^-)$, $M^+$ and iv) alkoxy, with $M^+$ as defined previously;
optionally substituted heteroaryl; preferentially a benzothiazolyl group;
cycloalkyl; in particular cyclohexyl;
Ar—N=N— with Ar representing an optionally substituted aryl group; preferentially a phenyl optionally substituted with one or more alkyl, $(O)_2S(O-)$—, M+ or phenylamino groups; or
or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O-)$—, M+; iv) hydroxyl; v) mercapto;

vi) (di)(alkyl)amino; vii) R°—C(X)—X'—; viii) R°—X'—C(X)—; ix) R°—X'—C(X)—X"—; x) Ar—N=N— and xi) optionally substituted aryl (alkyl)amino; with $M^+$, R°, X, X', X" and Ar previously defined; and W represents a sigma bond 6, an oxygen or sulfur atom, or a divalent radical i) —NR—, with R as defined previously, or ii) methylene —C($R_a$)($R_b$)—, with $R_a$ and $R_b$, which may be identical or different, representing a hydrogen atom or an aryl group, or alternatively $R_a$ and $R_b$ form, with the carbon atom that bears them, a spiro cycloalkyl; preferentially, W represents a sulfur atom or $R_a$ and $R_b$ together form a cyclohexyl;

with the understanding that formulae (II) and (Ill) comprise at least one sulfonate radical $(O)_2S(O^-)$—, $M^+$ or one carboxylate radical $(O)CO^-$—, $M^+$ on one of the rings A, A', B, B' or C; preferentially sodium sulfonate.

As non-limiting examples of dyes of formula (II), mention may be made of Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2 and Food yellow 3 or sunset yellow.

As non-limiting examples of dyes of formula (III), mention may be made of Acid Red 111, Acid Red 134 and Acid yellow 38.

In another exemplary embodiment, the anionic hair dyeing agent may be chosen from the pyrazolone anionic azo dyes of formulae (IV) and (V):

wherein:
$R_{11}$, $R_{12}$ and $R_{13}$, which may be identical or different, represent a hydrogen or halogen atom, an alkyl group or —$(O)_2S(O^-)$, $M^+$ with $M^+$ as defined previously;

$R_{14}$ represents a hydrogen atom, an alkyl group or a group —C(O)O—, M+ with M as defined previously;

$R_{15}$ represents a hydrogen atom;

$R_{16}$ represents an oxo group, in which case $R'_{16}$ is absent, or alternatively $R_{15}$ with $R_{16}$ together form a double bond;

$R_{17}$ and $R_{18}$, which may be identical or different, represent a hydrogen atom, or a group chosen from: $(O)_2S(O^-)$—, $M^+$ with $M^+$ as defined previously; Ar—O—S(O)$_2$— with Ar representing an optionally substituted aryl group, preferentially a phenyl optionally substituted with one or more alkyl groups;

$R_{19}$ and $R_{20}$ together form either a double bond, or a benzo group D', which is optionally substituted;

$R'_{16}$, $R'_{19}$ and $R'_{20}$, which may be identical or different, represent a hydrogen atom or an alkyl or hydroxyl group;

$R_{21}$ represents a hydrogen atom or an alkyl or alkoxy group;

$R_a$ and $R_b$, which may be identical or different, are as defined previously, preferentially $R_a$ represents a hydrogen atom and $R_b$ represents an aryl group;

Y represents either a hydroxyl group or an oxo group;

----- represents a single bond when Y is an oxo group; and represents a double bond when Y represents a hydroxyl group;

with the understanding that that formulae (IV) and (V) comprise at least one sulfonate radical $(O)_2S(O^-)$—, $M^+$ or one carboxylate radical $C(O)O^-$—, $M^+$ on one of the rings D or E; preferentially sodium sulfonate.

As non-limiting examples of dyes of formula (IV), mention may be made of Acid Red 195, Acid Yellow 23, Acid Yellow 27 and Acid Yellow 76.

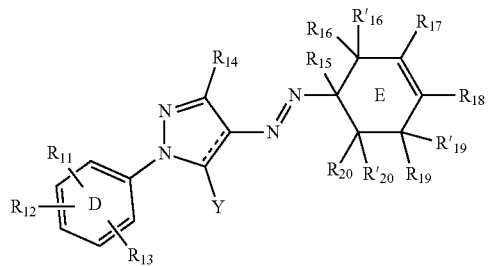

(IV)

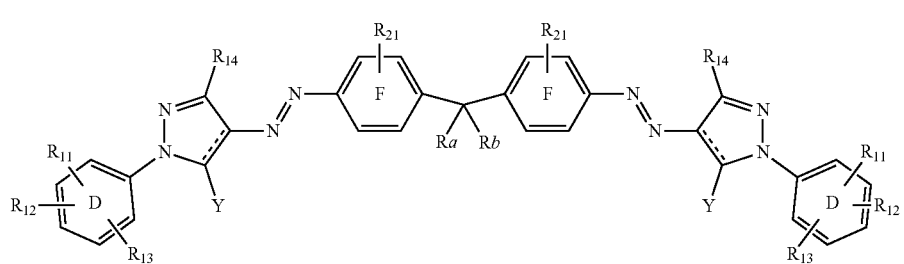

(V)

As a non-limiting example of a dye of formula (V), mention may be made of Acid Yellow 17.

In another exemplary embodiment, the anionic hair dyeing agent may be chosen from the anthraquinone dyes of formulae (VI) and (VII):

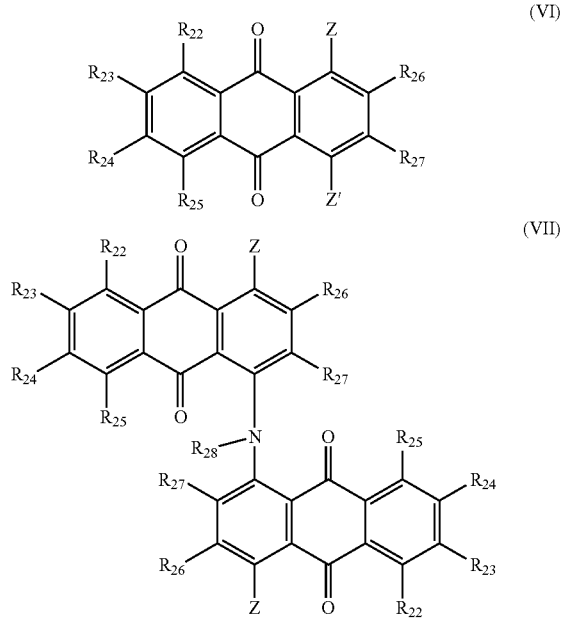

with the understanding that formulae (VI) and (VII) comprise at least one sulfonate radical $(O)_2S(O^-)$—, $M^+$ or a carboxylate radical $C(O)O^-$—, M+; preferentially sodium sulfonate.

As non-limiting examples of dyes of formula (VI), mention may be made of Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3, and EXT violet No 2.

As a non-limiting example of a dye of formula (VII), mention may be made of Acid Black 48.

In another exemplary embodiment, the anionic hair dyeing agent may be chosen from the nitro dyes of formulae (VIII) and (IX):

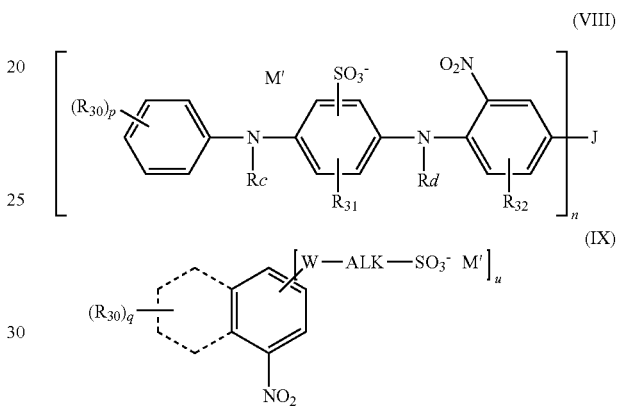

wherein:
$R_{22}$, $R_{23}$, $R_{24}$, $R_{25}$, $R_{26}$, and $R_{27}$, which may be identical or different, represent a hydrogen or halogen atom, or a group chosen from:
alkyl;
hydroxyl, mercapto;
alkoxy, alkylthio;
optionally substituted aryloxy or arylthio, preferentially substituted with one or more groups chosen from alkyl and $(O)_2S(O^-)$—, $M^+$ with $M^+$ as defined previously;
aryl(alkyl)amino optionally substituted with one or more groups chosen from alkyl and $(O)_2S(O^-)$—, $M^+$ with $M^+$ as defined previously;
(di)(alkyl)amino;
(di)(hydroxyalkyl)amino;
$(O)_2S(O^-)$—, $M^+$ with $M^+$ as defined previously;
Z' represents a hydrogen atom or a group $NR_{28}R_{29}$ with $R_{28}$ and $R_{29}$, which may be identical or different, representing a hydrogen atom or a group chosen from:
alkyl;
polyhydroxyalkyl such as hydroxyethyl;
aryl optionally substituted with one or more groups, more particularly i) alkyl such as methyl, n-dodecyl, n-butyl; ii) $(O)_2S(O^-)$—, $M^+$ with $M^+$ as defined previously; iii) $R°$—$C(X)$—$X'$—, $R°$—$X'$—$C(X)$—, $R°$—$X'$—$C(X)$—$X''$— with $R°$, X, X' and X" as defined previously, preferentially $R°$ represents an alkyl group;
cycloalkyl; e.g. cyclohexyl;
Z represents a group chosen from hydroxyl and $NR'_{28}R'_{29}$, with $R'_{28}$ and $R'_{29}$, which may be identical or different, representing the same atoms or groups as $R_{28}$ and $R_{29}$ as defined previously;

wherein:
$R_{30}$, $R_{31}$ and $R_{32}$, which may be identical or different, represent a hydrogen or halogen atom, or a group chosen from:
alkyl;
alkoxy optionally substituted with one or more hydroxyl groups, alkylthio optionally substituted with one or more hydroxyl groups;
hydroxyl, mercapto;
nitro, nitroso;
polyhaloalkyl;
$R°$—$C(X)$—$X'$—, $R°$—$X'$—$C(X)$—, $R°$—$X'$—$C(X)$—$X'$— with $R°$, X, X', and X" as defined previously;
$(O)_2S(O^-)$—, $M^+$ with $M^+$ as defined previously;
$(O)CO^-$—, $M^+$ with $M^+$ as defined previously;
(di)(alkyl)amino;
(di)(hydroxyalkyl)amino;
heterocycloalkyl such as piperidino, piperazino or morpholino;
$R_c$ and $R_d$, which may be identical or different, represent a hydrogen atom or an alkyl group;
W is as defined previously; for example W may represent an —NH— group;
ALK represents a linear or branched divalent $C_1$-$C_6$ alkylene group; more particularly, ALK represents a —$CH_2$—$CH_2$— group;
n is 1 or 2;
p represents an integer inclusively between 1 and 5;
q represents an integer inclusively between 1 and 4;
u is 0 or 1;

when n is 1, J represents a nitro or nitroso group;

when n is 2, J represents an oxygen or sulfur atom, or a divalent radical —S(O)$_m$— with m representing an integer 1 or 2; for example, J represents a radical —SO$_2$—;

M' represents a hydrogen atom or a cationic counterion;

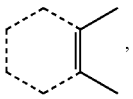

which may be present or absent, represents a benzo group optionally substituted with one or more R$_{30}$ groups as defined previously;

it being understood that formulae (VIII) and (IX) comprise at least one sulfonate radical (O)$_2$S(O$^-$)—, M$^+$ or a carboxylate radical C(O)O$^-$—, M; for example sodium sulfonate.

As non-limiting examples of dyes of formula (VIII), mention may be made of Acid Brown 13 and Acid Orange 3.

As non-limiting examples of dyes of formula (IX), mention may be made of Acid Yellow 1, the sodium salt of 2,4-dinitro-1-naphthol-7-sulfonic acid, 2-piperidino-5-nitrobenzenesulfonic acid, 2(4'-N,N(2''-hydroxyethyl)amino-2'-nitro)anilineethanesulfonic acid, 4-p-hydroxyethylamino-3-nitrobenzenesulfonic acid, and EXT D&C yellow 7.

In another exemplary embodiment, the anionic hair dyeing agent may be chosen from the triarylmethane dyes of formula (X):

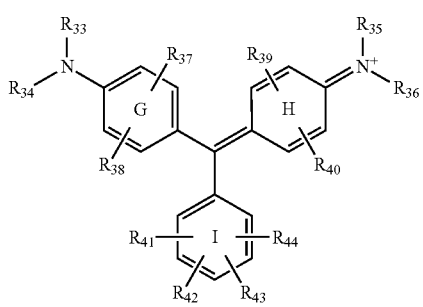

(X)

wherein:

R$_{33}$, R$_{34}$, R$_{35}$ and R$_{36}$, which may be identical or different, represent a hydrogen atom or a group chosen from alkyl, optionally substituted aryl and optionally substituted arylalkyl; particularly an alkyl and benzyl group optionally substituted with a group (O)$_m$S(O$^-$)—, M with M$^+$ and m as defined previously;

R$_{37}$, R$_{38}$, R$_{39}$, R$_{40}$, R$_{41}$, R$_{42}$, R$_{43}$ and R$_{44}$, which may be identical or different, represent a hydrogen atom or group chosen from:

alkyl;

alkoxy, alkylthio;

(di)(alkyl)amino;

hydroxyl, mercapto;

nitro, nitroso;

R°—C(X)—X'—, R°—X'—C(X)—, R°—X'—C(X)—X''— with R° representing a hydrogen atom or an alkyl or aryl group; X, X' and X'', which may be identical or different, representing an oxygen or sulfur atom, or NR with R representing a hydrogen atom or an alkyl group;

(O)$_2$S(O$^-$)—, M$^+$ with M$^+$ representing a hydrogen atom or a cationic counterion;

(O)CO$^-$—, M$^+$ with M$^+$ as defined previously;

or alternatively two contiguous groups R$_{41}$ with R$_{42}$ or R$_{42}$ with R$_{43}$ or R$_{43}$ with R$_{44}$ together form a fused benzo group: I'; with I' optionally substituted with one or more groups chosen from i) nitro; ii) nitroso; iii) (O)$_2$S(O$^-$)—, M$^+$; iv) hydroxyl; v) mercapto; vi) (di)(alkyl)amino; vii) R°—C(X)—X'—; viii) R°—X'—C(X)—; ix) R°—X'—C(X)—X''—; with M$^+$, R°, X, X' and X'' as defined previously;

with the understanding that at least one of the rings G, H, I or I' comprises at least one sulfonate radical (O)$_2$S(O$^-$)— or a carboxylate radical —C(O)O—; for example sulfonate.

In a preferred embodiment of formula (X), R$_{37}$ to R$_{40}$ represent a hydrogen atom, and R$_{41}$ to R$_{44}$, which may be identical or different, represent a hydroxyl group or (O)$_2$S(O$^-$)—, M$^+$; and when R$_{43}$ with R$_{44}$ together form a benzo group, it is preferentially substituted with an (O)$_2$S(O$^-$)— group.

As non-limiting examples of dyes of formula (X), mention may be made of Acid Blue 1; Acid Blue 3; Acid Blue 7, Acid Blue 9; Acid Violet 49; Acid Green 3; Acid Green 5 and Acid Green 50.

In another exemplary embodiment, the anionic hair dyeing agent may be chosen from the xanthene-based dyes of formula (XI):

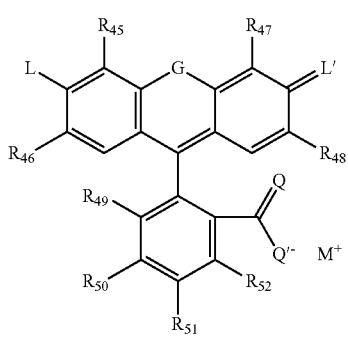

(XI)

wherein:

R$_{45}$, R$_{46}$, R$_{47}$ and R$_{48}$, which may be identical or different, represent a hydrogen or halogen atom;

R$_{49}$, R$_{50}$, R$_{51}$ and R$_{52}$, which may be identical or different, represent a hydrogen or halogen atom, or a group chosen from:

alkyl;

alkoxy, alkylthio;

hydroxyl, mercapto;

nitro, nitroso;

(O)$_2$S(O$^-$)—, M$^+$ with M$^+$ representing a hydrogen atom or a cationic counterion;

(O)CO$^-$—, M$^+$ with M$^+$ as defined previously;

G represents an oxygen or sulfur atom or a group NR$_e$ with R$_e$ as defined previously;

L represents an alkoxide $O^-$, $M^+$; a thioalkoxide $S^-$, $M^+$ or a group $NR_f$, with $R_f$ representing a hydrogen atom or an alkyl group and $M^+$ as defined previously; $M^+$ is particularly sodium or potassium;

L' represents an oxygen or sulfur atom or an ammonium group: $N^+R_fR_g$, with $R_f$ and $R_g$, which may be identical or different, representing a hydrogen atom, an alkyl group or optionally substituted aryl; for example L' represents an oxygen atom or a phenylamino group optionally substituted with one or more alkyl or $(O)_mS(O^-)$—, $M^+$ groups with m and $M^+$ as defined previously;

Q and Q', which may be identical or different, represent an oxygen or sulfur atom; and $M^+$ is as defined previously.

As non-limiting examples of dyes of formula (XI), mention may be made of Acid Yellow 73; Acid Red 51; Acid Red 52; Acid Red 87; Acid Red 92; Acid Red 95 and Acid Violet 9.

In another exemplary embodiment, the anionic hair dyeing agent may be chosen from the indole-based dyes of formula (XII):

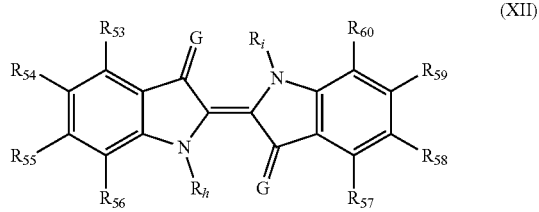

(XII)

wherein:

$R_{53}$, $R_{54}$, $R_{55}$, $R_{56}$, $R_{57}$, $R_{58}$, $R_{59}$ and $R_{60}$, which may be identical or different, represent a hydrogen atom or group chosen from:

alkyl;

alkoxy, alkylthio;

hydroxyl, mercapto;

nitro, nitroso;

$R°$—$C(X)$—$X'$—, $R°$—$X'$—$C(X)$—, $R°$—$X'$—$C(X)$—$X"$— with $R°$ representing a hydrogen atom or an alkyl or aryl group; X, X' and X", which may be identical or different, representing an oxygen or sulfur atom, or NR with R representing a hydrogen atom or an alkyl group;

$(O)_2S(O^-)$—, $M^+$ with $M^+$ representing a hydrogen atom or a cationic counterion;

$(O)CO^-$—, $M^+$ with $M^+$ as defined previously;

G represents an oxygen or sulfur atom or a group $NR_e$ with $R_e$ as defined previously;

$R_i$ and $R_h$, which may be identical or different, represent a hydrogen atom or an alkyl group;

it being understood that formula (XII) comprises at least one sulfonate radical $(O)_2S(O^-)$—, $M^+$ or a carboxylate radical —$C(O)O$—, $M^+$; for example sodium sulfonate.

As a non-limiting example of a dye of formula (XII), mention may be made of Acid Blue 74.

In another exemplary embodiment, the anionic hair dyeing agent may be chosen from the quinoline-based dyes of formula (XIII):

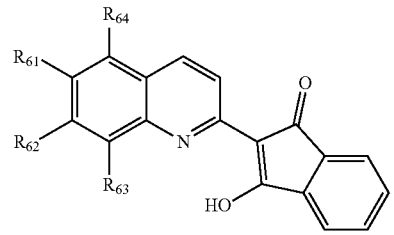

(XIII)

wherein:

$R_{61}$ represents a hydrogen or halogen atom or an alkyl group;

$R_{62}$, $R_{63}$, and $R_{64}$, which may be identical or different, represent a hydrogen atom or a group $(O)_2S(O^-)$—, $M^+$ with $M^+$ representing a hydrogen atom or a cationic counterion;

or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;

it being understood that formula (XIII) comprises at least one sulfonate radical $(O)_2S(O^-)$—, for example sodium sulfonate.

As non-limiting examples of dyes of formula (XIII), mention may be made of Acid Yellow 2, Acid Yellow 3 and Acid Yellow 5.

Without limitation, exemplary anionic hair dyeing agents may be chosen from (C.I. 45380) Acid Red 87 (formula XI); (C.I. 10316) Sodium salt of 2,4-dinitro-1-naphthol-7-sulfonic acid (formula IX); (C.I. 10383) Acid Orange 3 (formula VIII); (C.I. 13015) Acid Yellow 9/Food Yellow 2 (formula II); (C.I. 14780) Direct Red 45/Food Red 13 (formula II); (C.I. 13711) Acid Black 52 (formula II); (C.I. 13065) Acid Yellow 36 (formula II); (C.I. 14700) Sodium salt of 1-hydroxy-2-(2',4'-xylyl-5-sulfonatoazo)naphthalene-4-sulfonic acid/Food Red 1 (formula II); (C.I. 14720) Acid Red 14/Food Red 3/Mordant Blue 79 (formula II); (C.I. 14805) Sodium salt of 4-hydroxy-3-[(2-methoxy-5-nitrophenyl)diaza]-6-(phenylamino)naphthalene-2-sulfonic acid/Acid Brown 4 (formula II); (C.I. 15510) Acid Orange 7/Pigment Orange 17/Solvent Orange 4 (formula II); (C.I. 15985) Food Yellow 3/Pigment Yellow 104 (formula II); (C.I. 16185) Acid Red 27/Food Red 9 (formula II); (C.I. 16230) Acid Orange 10/Food Orange 4 (formula II); (C.I. 16250) Acid Red 44 (formula II); (C.I. 17200) Acid Red 33/Food Red 12 (formula II); (C.I. 15685) Acid Red 184 (formula II); (C.I. 19125) Acid Violet 3 (formula II); (C.I. 18055) Sodium salt of 1-hydroxy-2-(4'-acetamidophenylazo)-8-acetamidonaphthalene-3,6-disulfonic acid/Acid Violet 7/Food Red 11 (formula II); (C.I. 18130) Acid Red 135 (formula II); (C.I. 19130) Acid Yellow 27 (formula IV); (C.I. 19140) Acid Yellow 23/Food Yellow 4 (formula IV); (C.I. 20170) 4'-(sulfonato-2",4"-dimethyl)bis(2,6-phenylazo)-1,3-dihydroxybenzene/Acid Orange 24 (formula II); (C.I. 20470) Sodium salt of 1-amino-2-(4'-nitrophenylazo)-7-phenylazo-8-hydroxy-naphthalene-3,6-disulfonic acid/Acid Black 1 (formula II); (C.I. 23266) (4-((4-methylphenyl)sulfonyloxy) phenylazo)-2,2'-dimethyl-4-((2-hydroxy-5,8-disulfonato) naphthylazo)biphenyl/Acid Red 111 (formula III); (C.I. 27755) Food Black 2 (formula II) (C.I. 25440) 1-(4'-sulfonatophenylazo)-4-((2"-hydroxy-3"-acetylamino-6",8"-disulfonato)naphthylazo)-6-sulfonatonaphthalene (tetrasodium salt)/Food Black 1 (formula II), (C.I. 42090) Acid Blue 9 (formula X) (C.I. 60730) Acid Violet 43 (formula VI) (C.I.

61570) Acid Green 25 (formula VI), (C.I. 62045) Sodium salt of 1-amino-4-cyclohexylamino-9,10-anthraquinone-2-sulfonic acid/Acid Blue 62 (formula VI), (C.I. 62105) Acid Blue 78 (formula VI), (C.I. 14710) Sodium salt of 4-hydroxy-3-((2-methoxyphenyl)azo)-1-naphthalenesulfonic acid/Acid Red 4 (formula II); 2-Piperidino-5-nitrobenzenesulfonic acid (formula IX); 2-(4'-N,N-(2"-Hydroxyethyl)amino-2'-nitro)anilineethanesulfonic acid (formula IX); 4-β-Hydroxyethylamino-3-nitrobenzenesulfonic acid (formula IX); (C.I. 42640) Acid Violet 49 (formula X); (C.I. 42080) Acid Blue 7 (formula X); (C.I. 58005) Sodium salt of 1,2-dihydroxy-3-sulfoanthraquinone/Mordant Red 3 (formula VI); (C.I. 62055) Sodium salt of 1-amino-9,10-dihydro-9,10-dioxo-4-(phenylamino) 2-anthracenesulfonic acid/Acid Blue 25 (formula VI); or (C.I. 14710) Sodium salt of 4-hydroxy-3-((2-methoxyphenyl)azo)-1-naphthalenesulfonic acid/Acid Red 4 (formula II).

Exemplary and non-limiting cationic dyes include the hydrazono cationic dyes of formulas (Va) and (V'a), the azo cationic dyes (VIa) and (VI'a) and the diazo cationic dyes (VIIa) below:

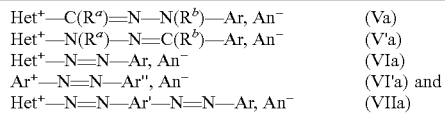

| | |
|---|---|
| Het⁺—C(Rᵃ)=N—N(Rᵇ)—Ar, An⁻ | (Va) |
| Het⁺—N(Rᵃ)—N=C(Rᵇ)—Ar, An⁻ | (V'a) |
| Het⁺—N=N—Ar, An⁻ | (VIa) |
| Ar⁺—N=N—Ar", An⁻ | (VI'a) and |
| Het⁺—N=N—Ar'—N=N—Ar, An⁻ | (VIIa) | in which:
Het+ represents a cationic heteroaryl radical, preferably bearing an endocyclic cationic charge, such as imidazolium, indolium or pyridinium, optionally substituted preferentially with one or more (C1-C8) alkyl groups such as methyl;
Ar+ representing an aryl radical, such as phenyl or naphthyl, bearing an exocyclic cationic charge, preferentially ammonium, particularly tri(C1-C8)alkylammonium such as trimethylammonium;
Ar represents an aryl group, especially phenyl, which is optionally substituted, preferentially with one or more electron-donating groups such as i) optionally substituted (C1-C8)alkyl, ii) optionally substituted (C1-C8)alkoxy, iii) (di)(C1-C8)(alkyl)amino optionally substituted on the alkyl group(s) with a hydroxyl group, iv) aryl(C1-C8)alkylamino, v) optionally substituted N—(C1-C8)alkyl-N-aryl(C1-C8)alkylamino or alternatively Ar represents a julolidine group;
Ar' is an optionally substituted divalent (hetero)arylene group such as phenylene, particularly para-phenylene, or naphthalene, which are optionally substituted, preferentially with one or more groups (C1-C8)alkyl, hydroxyl or (C1-C8)alkoxy;
Ar" is an optionally substituted (hetero)aryl group such as phenyl or pyrazolyl, which are optionally substituted, preferentially with one or more groups (C1-C8)alkyl, hydroxyl, (di)(C1-C8)(alkyl)amino, (C1-C8)alkoxy or phenyl;
Ra and Rb, which may be identical or different, represent a hydrogen atom or a group (C1-C8)alkyl, which is optionally substituted, preferentially with a hydroxyl group;
or alternatively the substituent Ra with a substituent of Het+ and/or Rb with a substituent of Ar and/or Ra with Rb form, together with the atoms that bear them, a (hetero)cycloalkyl;
particularly, Ra and Rb represent a hydrogen atom or a group (C1-C4)alkyl, which is optionally substituted with a hydroxyl group; and
An- represents an anionic counter-ion such as mesylate or halide.

For example, useful cationic dyes may be chosen from Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples of nonionic hydrophobic direct dyes may be chosen from HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15.

Natural hair dyeing agents may also be chosen. As used herein, the term "natural" hair dyeing agents include dyes derived from natural materials (plant, mineral or animal origin), for instance extracts, ground material and decoctions, which have a greater or smaller concentration of dyes. Without being limiting, exemplary natural hair dyeing agents may be chosen from orceins, curcumin, indole derivatives such as isatin or indole-2,3-dione, indigoids including indigo, phthalocyanines, and porphyrins optionally complexed to a metal, glycosyl or non-glycosyl iridoids, chromene dyes, anthraquinone and naphthoquinone dyes such as lawsone or henna, juglone, spinulosin, chromene or chroman dyes, such as neoflavanols and neoflavanones, flavanols, and anthocyanidols. Use may also be made of extracts containing these natural dyes, for example plant extracts or poultices containing said dyes. In some embodiments, the dye comprises, consists essentially of, or consists of one or more natural dyes, preferably hydrophobic natural dyes. For example, the dye may comprise, consist essentially of, or consist of curcumin, indigo, or a mixture thereof.

In various exemplary embodiments, the microtubes may be loaded with an amount of hair dyeing agent ranging from about 0.01% to about 50% by weight, based on the weight of the microtube prior to loading, such as about 0.1% to about 50%, about 0.1% to about 45%, about 0.1% to about 40%, about 0.1% to about 35%, about 0.1% to about 30%, about 0.1% to about 25%, about 0.1% to about 20%, about 0.1% to about 15%, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.5% to about 50%, about 0.5% to about 45%, about 0.5% to about 40%, about 0.5% to about 35%, about 0.5% to about 30%, about 0.5% to about 25%, about 0.5% to about 20%, about 0.5% to about 15%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2% by weight, based on the weight of the microtube prior to loading, including all subranges thereof.

For example, in certain embodiments, the microtubes may be loaded with an amount of hair dyeing agent ranging from about 30% to about 50% by weight, based on the weight of the microtube prior to loading, such as about 35% to about 50%, about 40% to about 50%, about 30% to about 45%, about 35% to about 45%, or about 40% to about 45% by weight, based on the weight of the microtube prior to loading, including all subranges thereof.

In other exemplary embodiments, the microtubes may be loaded with an amount of hair dyeing agent ranging from about 0.01% to about 10% by weight, based on the weight of the microtube prior to loading, such as about 0.01% to about 7.5%, about 0.01% to about 5%, about 0.01% to about 3.5%, about 0.1% to about 10%, about 0.1% to about 7.5%, about 0.1% to about 5%, about 0.1% to about 3.5%, about 1% to about 10%, about 1% to about 7.5%, about 1% to about 5%, or about 1% to about 3.5% by weight, based on the weight of the microtube prior to loading, including all subranges thereof.

The dyeing composition typically comprises a solvent, in which the microtube-dye composite may be dispersed. The solvent may be chosen from water, non-aqueous solvents, or a mixture thereof. The solvent will advantageously be chosen so that it will not interfere with deposition of the microtube-dye composite on the hair, and that it will not damage or irritate the hair, scalp, and/or skin. In various embodiments, the solvent comprises, consists essentially of, or consists of water.

Exemplary non-aqueous solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, and mixtures thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. The organic solvents can be volatile or non-volatile compounds.

Further non-limiting examples of solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and mixtures thereof.

The solvent may be present in the dyeing composition in an amount ranging from about 50% to about 99.99% by weight, relative to the total weight of the dyeing composition. For example, the total amount of solvent may range from about 80% to about 99%, about 80% to about 98%, about 80% to about 97%, about 80% to about 96%, about 80% to about 95%, about 80% to about 94%, about 80% to about 93%, about 80% to about 92%, about 80% to about 91%, or about 80% to about 90% by weight, relative to the total weight of the dyeing composition.

The dyeing composition may comprise additional components, as long as such additional components do not substantially interfere with the deposition of the microtube-dye composite onto the hair. By way of example only, the dyeing composition may comprise pH adjusters, preservatives, humectants, oils, fragrances, etc.

In various embodiments, the dyeing composition has a pH of less than or equal to about 7, such as less than or equal to about 6, less than or equal to about 5, less than or equal to about 4, or less than or equal to about 3. For example, the pre-treatment composition may have a pH ranging from about 1 to about 7, such as from about 2 to about 6, from about 2.5 to about 5, or from about 3 to about 4.

The microtube-dye composite may be present in the dyeing composition in an amount ranging from about 0.01% to about 15% by weight, based on the weight of the dyeing composition, such as about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2% by weight, based on the weight of the dyeing composition, including all subranges thereof.

It should be understood that the microtube-dye composite included in the dyeing composition can include mixtures of different microtubes, mixtures of different dyes, or both. By way of example only, a first set of microtubes comprising halloysite may be loaded with one dye, a second set of microtubes comprising halloysite may be loaded with a second dye, and the first and second sets of microtube-dye composites may be included in the dyeing composition. As a further example, a first set of microtubes comprising halloysite may be loaded with one dye, a second set of microtubes comprising a structure other than halloysite may be loaded with a second dye, and the first and second sets of microtube-dye composites may be included in the dyeing composition.

Methods

It has been discovered that altering the color of the hair using systems according to the disclosure has the surprising and unexpected benefit of imparting improved color deposition and vibrancy. In particular, while it was previously discovered that microtube-dye composites can be used to impart color to hair with less damage to the hair and/or less skin and/or scalp irritation, systems and methods according to the disclosure provide surprisingly significant improvement of deposition of color and vibrancy compared to use of the microtube-dye composite alone.

Methods according to the disclosure include treating the hair with the pre-treatment composition and treating the hair with the dyeing composition.

In various methods according to the disclosure, the hair is first treated with the pre-treatment composition by applying the pre-treatment composition to the hair and optionally massaging or combing the composition throughout the hair to ensure complete coverage. The pre-treatment composition may be applied to the hair in any desired amount, for example up to about 10 grams of pre-treatment composition per gram of hair, such as up to about 5 grams per gram of hair, up to about 4 grams per gram of hair, up to about 3 grams per gram of hair, up to about 2 grams per gram of hair, or up to about 1 gram per gram of hair.

The pre-treatment composition may optionally be left on the hair for a period of time, for example ranging up to about 60 minutes or up to about 45 minutes, such as about 30 seconds to about 60 minutes, about 1 minute to about 50 minutes, about 3 minutes to about 40 minutes, or about 5 minutes to about 30 minutes. The pre-treatment composition may optionally be partially, completely, or substantially completely removed from the hair after the leave-on period, and the hair may optionally be subsequently partially, completely, or substantially completely dried, e.g. with a blow dryer or hood or air dried. Alternatively, the hair may be partially, completely, or substantially completely dried, e.g. with a blow dryer or hood or air dried, without removing the pre-treatment composition from the hair, for example without rinsing the hair or without towel-drying the hair. Preferably, the hair is completely or substantially completely dried after a leave-in period without removing the pre-treatment composition from the hair, wherein the step of drying optionally includes the use of heat.

The methods further include a step of applying the dyeing composition to the hair after the pre-treatment composition is applied to the hair and optionally dried, for example by massaging or combing the composition throughout the hair to ensure complete coverage. The dyeing composition, which includes a microtube-dye composite, e.g. a halloysite-dye composite, may be applied to the hair in any desired amount, for example up to about 10 grams of dyeing composition per gram of hair, such as up to about 5 grams per gram of hair, up to about 4 grams per gram of hair, up to about 3 grams per gram of hair, up to about 2 grams per gram of hair, or up to about 1 gram per gram of hair.

The dyeing composition may be left on the hair for a period of time to achieve a desired coloration effect, for example ranging up to about 60 minutes or up to about 45 minutes, such as about 30 seconds to about 60 minutes, about 1 minute to about 50 minutes, about 3 minutes to about 40 minutes, or about 5 minutes to about 30 minutes. One skilled in the art will be able to determine an appropriate amount of time to leave the dyeing composition on the hair in order to achieve the desired effect.

After a desired leave-in period, the dyeing composition may be rinsed from the hair, and the hair may optionally be washed, rinsed, dried, and/or styled in any conventional manner.

In various embodiments, the above-described steps of applying a pre-treatment composition to the hair, optionally leaving the pre-treatment composition on the hair for a leave-in period, optionally removing the pre-treatment composition from the hair, applying a dyeing composition to the hair, optionally leaving the dyeing composition on the hair for a leave-in period, and optionally removing the dyeing composition from the hair may be repeated one or more times, with the same or different pre-treatment and/or dyeing composition(s).

Thus, by way of example only, one method according to the disclosure may comprise applying a pre-treatment composition (1a) to the hair, leaving the pre-treatment composition (1a) on the hair for a leave-in period, removing the pre-treatment composition (1a) from the hair, applying a dyeing composition (1b) to the hair, leaving the dyeing composition (1b) on the hair for a leave-in period, and removing the dyeing composition (1b) from the hair.

Another exemplary method according to the disclosure may comprise applying a pre-treatment composition (1a) to the hair, leaving the pre-treatment composition (1a) on the hair for a leave-in period, removing the pre-treatment composition (1a) from the hair, applying a dyeing composition (1b) to the hair, leaving the dyeing composition (1b) on the hair for a leave-in period, removing the dyeing composition (1b) from the hair, applying the pre-treatment composition (1a) to the hair a second time, leaving the pre-treatment composition (1a) on the hair for a leave-in period, removing the pre-treatment composition (1a) from the hair, applying the dyeing composition (1b) to the hair a second time, leaving the dyeing composition (1b) on the hair for a leave-in period, and removing the dyeing composition (1b) from the hair, where pre-treatment composition (1a) in the first application is identical to pre-treatment composition (1a) in the second application, and dyeing composition (1b) in the first application is identical to dyeing composition (1b) in the second application.

Yet another exemplary method according to the disclosure may comprise applying a pre-treatment composition (1a) to the hair, leaving the pre-treatment composition (1a) on the hair for a leave-in period, removing the pre-treatment composition (1a) from the hair, applying a dyeing composition (1b) to the hair, leaving the dyeing composition (1b) on the hair for a leave-in period, removing the dyeing composition (1b) from the hair, applying a pre-treatment composition (2a) to the hair, leaving the pre-treatment composition (2a) on the hair for a leave-in period, removing the pre-treatment composition (2a) from the hair, applying a dyeing composition (2b) to the hair, leaving the dyeing composition (2b) on the hair for a leave-in period, and removing the dyeing composition (2b) from the hair, where pre-treatment compositions (1a) and (2a) are not identical, and hair dyeing compositions (1b) and (2b) are not identical.

A further exemplary and non-limiting method according to the disclosure may comprise applying a pre-treatment composition (1a) to the hair, optionally drying the hair, applying a dyeing composition (1b) to the hair without first removing the pre-treatment composition (1a), optionally leaving the dyeing composition (1b) on the hair for a leave-in period, and removing the pre-treatment composition (1) and dyeing composition (1b) from the hair.

Kits

In a further embodiment, the disclosure relates to kits comprising the systems described herein. According to various embodiments, the kits may be multi-compartment or multi-container kits, where the compartments or containers are mutually separate. For example, the kits may comprise at least two compartments or containers, with a first compartment or container containing a pre-treatment composition according to the disclosure and a second compartment or container containing a dyeing composition according to the disclosure. In further embodiments, the kits may comprise at least three, at least four, or more compartments or containers.

The compartments or containers of kits according to the disclosure can be in any configuration, without limitation. For example, they can be a bottle, a tube, a sachet, an ampoule, or any other container configured to contain the pre-treatment composition(s) and dyeing composition(s) mutually separately in the kit. Kits may optionally include additional compartments for additional components, such as, for example, additional pre-treatment compositions, additional dyeing compositions, shampoo compositions, and the like.

Various exemplary embodiments of kits according to the disclosure comprise:
  a first compartment or container containing a pre-treatment composition comprising at least one amine-based compound and optionally at least one solvent; and
  a second compartment or container containing a dyeing composition comprising at least one microtube-dye composite and optionally at least one solvent, wherein, in the microtube-dye composite, the dye comprises at least one hair dyeing agent.

In yet further exemplary embodiments, kits according to the disclosure comprise:
  a first compartment or container containing a pre-treatment composition comprising from about 0.01% to about 15% of at least one non-surface active amine-based compound and water,
    wherein the pre-treatment composition has a pH of less than or equal to about 7, such as from about 2 to about 6; and
  a second compartment or container containing a dyeing composition comprising from about 0.01% to about 15% of at least one halloysite-dye composite comprising at least one hair dyeing agent and water,
    wherein the dyeing composition has a pH of less than or equal to about 7, such as from about 2 to about 6.

In various embodiments, kits such as those described above may optionally comprise additional compartments or containers, for example a third compartment or container containing a pre-treatment composition according to the disclosure different from that in the first compartment or container, and/or a fourth compartment or container containing a dyeing composition according to the disclosure different from that in the second compartment or container.

It is to be understood that, in exemplary kits according to the disclosure, the pre-treatment composition(s) and dyeing composition(s) can be as described herein for various systems, methods, and examples, for example with regard to particular components and/or ranges thereof.

Thus, in some embodiments, the pre-treatment and/or dyeing composition may not be present in the kit in a solvent, or may be present in the kit in a solvent but in concentrated form. For example, the pre-treatment and/or dyeing composition may be present in the kit in solid or powder form, and the user may mix the solid or powder with a solvent, such as water, prior to use. Alternatively, the pre-treatment and/or dyeing composition may be present in the form of a gel or thickened liquid that is to be mixed with a solvent, such as water, prior to use. In such embodiments, a kit with more than two compartments or containers may be envisioned. For example, a kit with three (and/or four) compartments or containers, where a third (and/or fourth) compartment or container includes a solvent, e.g. to mix with the pre-treatment composition and/or dyeing composition, may be chosen.

Kits may also include additional components or compartments, such as, for example, instructions or an apparatus or tool for applying the pre-treatment and/or dyeing compositions onto the hair, e.g. an applicator brush, and/or a compartment for the same.

As used herein, the terms "comprising," "having," and "including" (or "comprise," "have," and "include") are used in their open, non-limiting sense.

The terms "a," "an," and "the" are understood to encompass the plural as well as the singular.

The term "and/or" should be understood to include both the conjunctive and the disjunctive. For example, "A and/or B" means "A and B" as well as "A or B," and expressly covers instances of either without reference to the other. For example, "preventing and/or reducing" corrosion includes instances of preventing corrosion and reducing corrosion, as well as instances where corrosion is reduced but not prevented, etc.

As used herein, the phrases "and mixtures thereof," "and a mixture thereof," "and combinations thereof," "and a combination thereof," "or mixtures thereof," "or a mixture thereof," "or combinations thereof," and "or a combination thereof," are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

As used herein, all ranges provided are meant to include every specific range within, and combination of sub ranges between, the given ranges. Thus, a range from 1-5, includes specifically 1, 2, 3, 4, and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

As used herein, "free" means that the component or property is not detectable using accepted methodologies, and "substantially" or "essentially" free means that the component or property, while detectable using accepted methodologies, is negligible.

It is to be understood that the use of the terms "treat," "treated," "treatment," and variations thereof is not intended to be limiting, but rather is merely intended to indicate that one or more compositions is applied to the hair, and optionally removed from the hair, as described herein. For example, hair that is "treated" with a pre-treatment composition according to the disclosure may have had the pre-treatment composition applied, and/or may have had the pre-treatment composition applied and removed, e.g. by rinsing or towel drying. As a further example, hair that is "treated" with a dyeing composition according to the disclosure may have had the dyeing composition applied, and/or may have had the dyeing composition applied and rinsed from the hair. As yet a further example, hair that is "treated" with a system according to the disclosure may have had the pre-treatment composition applied and optionally removed, and additionally may have had the dyeing composition applied and optionally rinsed from the hair.

By "non-surface active amine" it is meant that the amine compounds are not amine-based surfactants in the compositions in which they are present. By way of non-limiting example only, in some embodiments, the "non-surface active amines" are not capable of depressing the surface tension of deionized water under standard conditions to a value of less than about 50 mN/m, when added to deionized water in a concentration by weight of 0.5-1%.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The examples that follow serve to illustrate embodiments of the present disclosure without, however, being limiting in nature. It will be apparent to those skilled in the art that various modifications and variations can be made in the delivery system, compositions, and methods of the invention without departing from the spirit or scope of the invention.

EXAMPLES

Implementation of various non-limiting embodiments of the disclosure is demonstrated by way of the following Examples.

In the Examples, the change in the color of hair is evaluated with the L*a*b* system, using Colorshot MS, where the change is determined by evaluating the color of the hair after treatment compared to the color of the hair before treatment. The change in color ($\Delta E$) is defined as:

The greater the value for $\Delta E$, the greater the difference in color of treated hair relative to the color of the hair prior to treatment.

Example 1—Microtube-Dye Composites

The procedures of Examples 1A and 1B below were followed to prepare microtube-dye composites having the dye loadings shown in Table 1.

TABLE 1

| | Composite | Dye loading |
|---|---|---|
| $H\text{-}C_{(1.4)}$ | Halloysite-Curcumin | 1.4% |
| $H\text{-}C_{(3)}$ | Halloysite-Curcumin | 3% |
| $H\text{-}I_{(43)}$ | Halloysite-Indigo | 43% |

Example 1A—Halloysite-Curcumin Composites

Curcumin was completely dissolved in acetone (10 mg dye per mL acetone) and unmodified halloysite was added (weight ratio of dye:halloysite ~2:1) with stirring. The dispersion was sonicated for about five minutes and then vacuumed and stirred overnight. After centrifuging for about five minutes at 5000 rpm, the supernatant was discarded and the sample was dried under vacuum and crushed into a fine powder.

Example 1B—Halloysite-Indigo Composites

Indigo was completely dissolved in water (99.99% water with 0.01% sodium carbonate; 5 mg dye per mL solvent) and unmodified halloysite was added (weight ratio of dye: halloysite ~2:1) with stirring. The dispersion was sonicated for about five minutes and then vacuumed and stirred overnight. After centrifuging for about five minutes at 5000 rpm, the supernatant was discarded and the sample was dried under vacuum and crushed into a fine powder.

Example 2—Pre-treatment Compositions

The pre-treatment compositions in Table 2 were prepared by dissolving the amine-based compound in water and adjusting the pH of the solution with sodium hydroxide and/or hydrochloric acid, as needed, to prepare aqueous compositions having the reported concentrations of amine-based compounds and pH values.

TABLE 2

| Pre-treatment composition | Amine compound | Molecular weight | pH | Concentration |
|---|---|---|---|---|
| 2A | polyethyleneimine | 800 | 3 | 3.33% |
| 2B | polyethyleneimine | 1300 | 3 | 0.5% |
| 2C | polyethyleneimine | 1300 | 3 | 3.33% |
| 2D | polyethyleneimine | 1300 | 3 | 10% |
| 2E | polyethyleneimine | 1300 | 7 | 3.33% |
| 2F | polyethyleneimine | 1300 | 11 | 3.33% |
| 2G | polyethyleneimine | 2000 | 3 | 3.33% |
| 2H | polyethyleneimine | 25,000 | 3 | 3.33% |
| 2I | arginine | 174.2 | 3 | 3% |

Example 3—Dyeing Compositions

The dyeing compositions in Table 3 were prepared by dispersing the specified halloysite-dye composites from Table 1 in water and adjusting the pH of the dispersion with sodium hydroxide and/or hydrochloric acid, as needed, to prepare aqueous compositions having the reported concentrations of halloysite-dye composites and pH values.

TABLE 3

| Dyeing composition | Halloysite-dye composite | pH | Concentration |
|---|---|---|---|
| 3A | $H\text{-}C_{(1.4)}$ | 3 | 2.5% |
| 3B | $H\text{-}C_{(1.4)}$ | 7 | 2.5% |
| 3C | $H\text{-}C_{(1.4)}$ | 7 | 5% |
| 3D | $H\text{-}C_{(3)}$ | 7 | 2.5% |
| 3E | $H\text{-}C_{(3)}$ | 3 | 5% |
| 3F | $H\text{-}C_{(3)}$ | 7 | 5% |
| 3G | $H\text{-}I_{(43)}$ | 3 | 2.5% |
| 3H | $H\text{-}I_{(43)}$ | 3 | 5% |
| 3I | $H\text{-}I_{(43)}$ | 7 | 5% |

Example 4—Demonstration of Benefit of Pre-Treatment

The following Examples 4-1 and 4-2 demonstrate the surprising improvement in color deposition on the hair using systems and methods according to the disclosure including pre-treatment with non-surface active amine-based compounds.

Example 4-1—Color Imparted by Systems Comprising Pre-Treatment Compositions and Dyeing Compositions (Inventive)

The color imparted to hair with systems 4A-4J comprising combinations of pre-treatment compositions prepared in Example 2 and dyeing compositions prepared in Example 3 as set forth in Table 4-1 was evaluated.

TABLE 4-1

| System | Pre-treatment composition | Dyeing composition | ΔE |
|---|---|---|---|
| 4A | 2C | 3F | 27.2 |
| 4B | 2C | 3A | 15.9 |
| 4C | 2E | 3B | 13.2 |
| 4D | 2C | 3H | 43.1 |
| 4E | 2C | 3I | 39.7 |
| 4F | 2F | 3I | 39.6 |
| 4G | 2I | 3D | 21.2 |
| 4H | 2A | 3D | 19.3 |
| 4I | 2B | 3D | 20.4 |
| 4J | 2D | 3D | 17.3 |

The process for treating hair with inventive systems 4A-4J was as follows. First, swatches of 90% grey virgin hair were rinsed with ~37° C. tap water (five passes), a commercial shampoo was applied and lathered for about 30 seconds, the swatch was allowed to rest for about one minute and then rinsed with tap water for about 30 seconds. The swatch was then allowed to air dry.

Once the swatch was completely dry, the pre-treatment composition was applied to the swatch at a ratio of about 2 grams of pre-treatment composition per 1 gram of hair and massaged through the hair for about one minute. The swatch was then combed with a wide-tooth comb for five passes and allowed to rest at room temperature for approximately 30 minutes. The swatch was then dried with a hair dryer set on high.

Once the swatch was completely dry, the dyeing composition was applied to the hair at a ratio of about 2 grams of dyeing composition per 1 gram of hair and massaged through the hair for about one minute. After a leave-in period of approximately 30 minutes at room temperature, the hair was rinsed with ~37° C. tap water. The hair was then dried with a hair dryer set on high.

The color change for each swatch was evaluated by determining the ΔE of the color of the hair after treatment compared to the color of the hair before treatment. The ΔE for each of systems 4A-4J is shown in Table 4-1 and FIGS. 1A-1D.

Example 4-2—Color Imparted by Dyeing Compositions Without Pre-Treatment (Comparative)

The color imparted to hair with dyeing compositions prepared in Example 3 and set forth in Table 4-2, without a pre-treatment step, was evaluated in order to determine the difference in color deposited on hair without a pre-treatment composition compared to color obtained with systems and methods including a pre-treatment composition.

TABLE 4-2

| Composition | Pre-treatment composition | Dyeing composition | ΔE |
|---|---|---|---|
| 4A' | — | 3F | 18.8 |
| 4B' | — | 3A | 12.3 |
| 4C' | — | 3B | 9.8 |
| 4D' | — | 3H | 40.4 |
| 4E' | — | 3I | 31.7 |
| 4F' | — | 3I | 31.7 |
| 4G' | — | 3D | 12.2 |

The process for treating hair with comparative compositions 4A'-4G' was as follows. First, swatches of 90% grey virgin hair were rinsed with ~37° C. tap water (five passes), a commercial shampoo was applied and lathered for about 30 seconds, the swatch was allowed to rest for about one minute and then rinsed with tap water for about 30 seconds. The swatch was then allowed to air dry.

Once the swatch was completely dry, the dyeing composition was applied to the hair at a ratio of about 2 grams of dyeing composition per 1 gram of hair and massaged through the hair for about one minute. After a leave-in period of approximately 30 minutes at room temperature, the hair was rinsed with ~37° C. tap water. The hair was then dried with a hair dryer set on high.

The color change for each swatch was evaluated by determining the ΔE of the color of the hair after treatment compared to the color of the hair before treatment. The ΔE for each of compositions 4A'-4G' is shown in Table 4-2 and FIGS. 1A-1D.

As seen in FIGS. 1A-1D, the hair treated with inventive systems 4A-4J shows significantly greater change in color relative to the color of the hair prior to treatment, when compared to the change in color of hair treated with comparative compositions 4A'-4G' not using a pre-treatment composition according to the disclosure.

Example 4 thus demonstrates that hair colored according to the disclosure, i.e. treated with a pre-treatment composition according to the disclosure and subsequently dyed with a dyeing composition according to the disclosure, surprisingly and unexpectedly leads to enhanced color deposition and more vibrant hair colors compared to hair not pre-treated as described herein.

Example 5—Demonstration of Benefit of Acidic pH

The following Examples 5-1 and 5-2 demonstrate the surprising improvement in color deposition on the hair using systems and methods where the pre-treatment and/or dyeing composition(s) is(are) acidic. The process for treating hair with systems 5A-5F was the same as described in Example 4-1.

Example 5-1—Color Imparted by Systems Comprising Acidic Pre-Treatment Compositions The color imparted to hair with systems 5A-5D comprising combinations of pre-treatment compositions prepared in Example 2 and dyeing compositions prepared in Example 3 as set forth in Table 5-1 was evaluated.

TABLE 5-1

| System | Pre-treatment composition | pH pre-treatment | Dyeing composition | pH dyeing | ΔE |
|---|---|---|---|---|---|
| 5A | 2E | 7 | 3B | 7 | 13.2 |
| 5B | 2C | 3 | 3B | 7 | 14.9 |
| 5C | 2F | 11 | 3G | 3 | 40.4 |
| 5D | 2C | 3 | 3G | 3 | 43.1 |

Figure 2A:
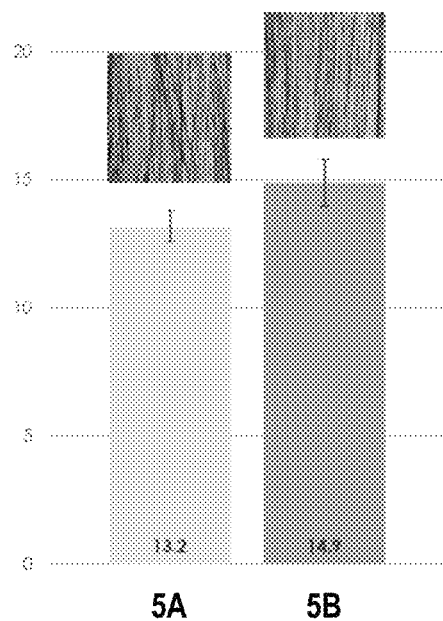
FIGS. 2A-2C are graphs demonstrating change in ΔE (y-axis) of hair treated with systems and methods of the disclosure using pre-treatment compositions according to exemplary embodiments of the disclosure having varying pH values, followed by dyeing compositions according to exemplary embodiments of the disclosure having varying pH values. These graphs demonstrate that systems according to the disclosure having lower pH of the pre-treatment and/or dyeing compositions surprisingly provide improved color deposition.
Figure 2B:
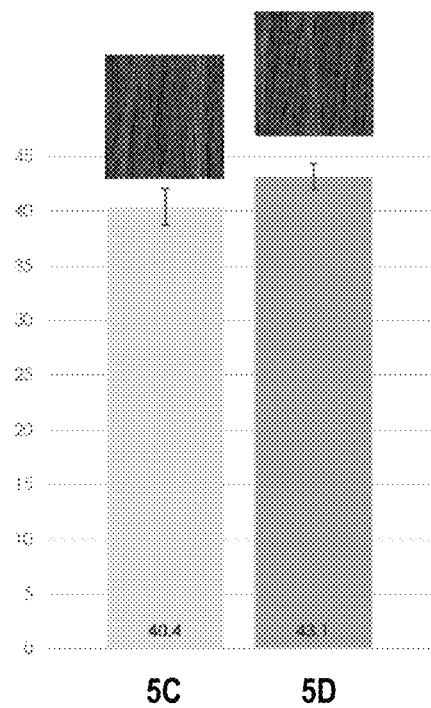

The color change for each swatch was evaluated by determining the ΔE of the color of the hair after treatment compared to the color of the hair before treatment. The ΔE for hair treated with each of systems 5A-5D is shown in Table 5-1 and FIGS. 2A-2B. As can be seen, the ΔE for hair treated with systems 5B and 5D (pre-treatment compositions having pH lower than 7) is greater than the ΔE for hair treated with systems 5A and 5C (identical systems but with corresponding pre-treatment compositions having pH of 7 or above).

Example 5-1 thus demonstrates that systems according to the disclosure comprising pre-treatment compositions having lower pH surprisingly provide greater change in color compared to systems comprising pre-treatment compositions having higher pH.

Example 5-2—Color Imparted by Systems Comprising Acidic Dyeing Compositions

The color imparted to hair by systems 5E-5F comprising combinations of pre-treatment composition 2C of Example 2 and dyeing compositions 3I or 3H Example 3 as set forth in Table 5-2 was evaluated.

TABLE 5-2

| System | Pre-treatment composition | pH pre-treatment | Dyeing composition | pH dyeing | ΔE |
|---|---|---|---|---|---|
| 5E | 2C | 3 | 3I | 7 | 39.7 |
| 5F | 2C | 3 | 3H | 3 | 43.1 |

Figure 2C:
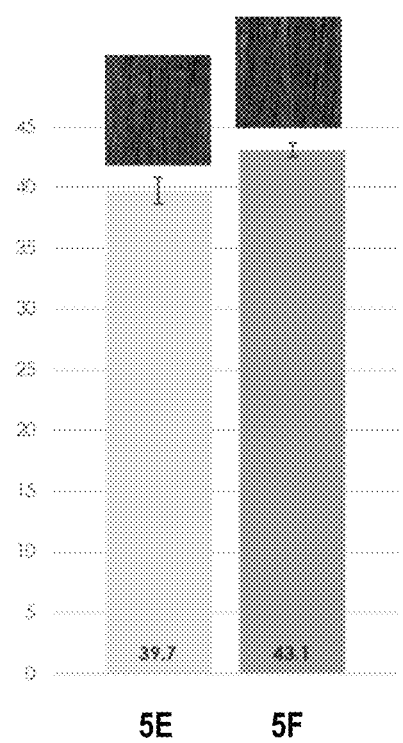

The color change for both swatches was evaluated by determining the ΔE of the color of the hair after treatment compared to the color of the hair before treatment. The ΔE for hair treated with systems 5E-5F is shown in Table 5-2 and FIG. 2C. As can be seen, the ΔE for hair treated with system 5F (dyeing composition having a pH lower than 7) is greater than the ΔE for hair treated with system 5E (identical system but with a dyeing composition having a pH of 7).

Example 5-2 shows that systems according to the disclosure having dyeing compositions with a lower pH surprisingly provide greater change in color compared to systems comprising dyeing compositions having higher pH.

Example 5 therefore demonstrates that hair colored according to the disclosure, treated with a pre-treatment composition having an acidic pH and subsequently dyed with a dyeing composition having an acidic pH, surprisingly and unexpectedly leads to enhanced color deposition and more vibrant hair color.

Example 6—Demonstration of Benefit of Molecular Weight of Amine Compound

The following Examples 6-1 and 6-2 demonstrate the surprising improvement in color deposition on the hair using systems and methods according to the disclosure. The process for treating hair with systems 6A-6C and C1 was the same as described in Example 4-1, and the process for treating hair with comparative compositions C2-C3 was the same as described in Example 4-2.

Example 6-1— Comparison of Color Imparted by Systems Comprising Pre-Treatment Compositions Having Polyethyleneimine of Different Molecular Weights The color imparted to hair with systems according to the disclosure comprising a combination of pre-treatment composition 2C of Example 2 and dyeing composition 3B of Example 3, and with comparative system C1 comprising a combination of pre-treatment composition 2H of Example 2 and dyeing composition 3B of Example 3, as set forth in Table 6-1, was evaluated. The color imparted to hair by comparative composition C2 was also evaluated, without a pre-treatment step.

TABLE 6-1

| System | Pre-treatment composition | Molecular weight of amine | pH pre-treatment | Dyeing composition | pH dyeing | ΔE |
|---|---|---|---|---|---|---|
| 6A | 2C | 1300 | 3 | 3B | 7 | 14.9 |
| C1 | 2H | 25,000 | 3 | 3B | 7 | 7 |
| C2 | — | — | — | 3B | 7 | 9.8 |

Figure 3A:
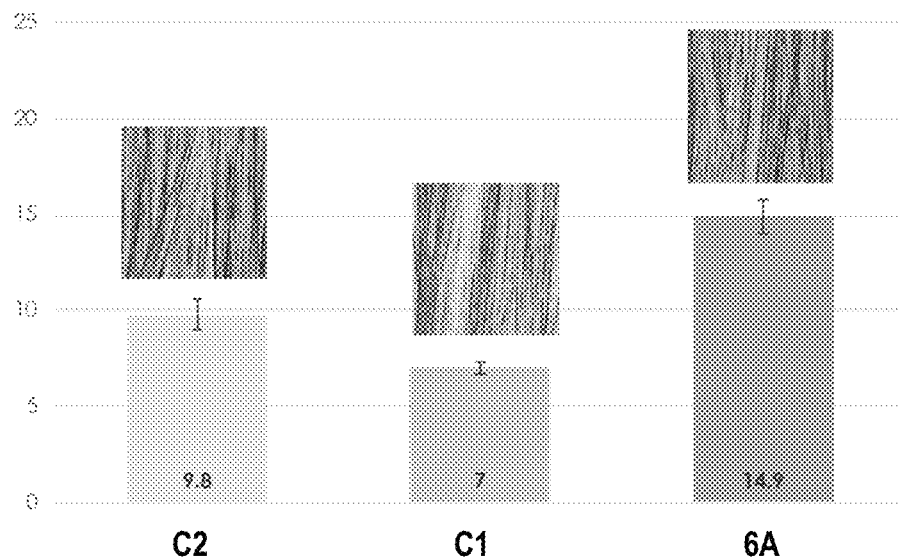
FIGS. 3A-3B are graphs demonstrating change in ΔE (y-axis) of hair treated with systems comprising exemplary pre-treatment compositions having polyethyleneimine of different molecular weights followed by dyeing compositions according to exemplary embodiments of the disclosure, or treated with dyeing compositions alone. These graphs demonstrate that pre-treatment compositions including non-surface active amine-based compounds having lower molecular weights surprisingly provide improved color deposition.

The color change for each swatch was evaluated by determining the ΔE of the color of the hair after treatment compared to the color of the hair before treatment. The ΔE for hair treated with systems 6A and C1, and composition C2, is shown in Table 6-1 and FIG. 3A. As can be seen, the ΔE for hair treated with system C1 (pre-treatment composition with polyethyleneimine having a molecular weight of 25,000) is lower than that of either hair treated with system 6A (pre-treatment composition with polyethyleneimine having a molecular weight of 1300) or with dyeing composition C2 with no pre-treatment.

Example 6-1 thus demonstrates that systems according to the disclosure comprising pre-treatment compositions having non-surface active amine-based compounds amine-based compounds with lower molecular weight surprisingly provide greater change in color compared to systems comprising pre-treatment compositions having amine-based compounds with higher molecular weight.

Example 6-2—Comparison of Color Imparted by Systems Comprising Pre-Treatment Compositions Having Polyethyleneimine of Different Molecular Weights The color imparted to hair with systems 6B and 6C comprising combinations of pre-treatment compositions 2G or 2A of Example 2 and dyeing composition 3D of Example 3 as set forth in Table 6-2 was evaluated. The color imparted to hair by comparative composition C3 was also evaluated, without a pre-treatment step.

TABLE 6-2

| System | Pre-treatment composition | Molecular weight of amine | pH pre-treatment | Dyeing composition | pH dyeing | ΔE |
|---|---|---|---|---|---|---|
| 6B | 2G | 2000 | 3 | 3D | 7 | 15.5 |
| 6C | 2A | 800 | 3 | 3D | 7 | 19.3 |
| C3 | — | — | — | 3D | 7 | 12.2 |

Figure 3B:
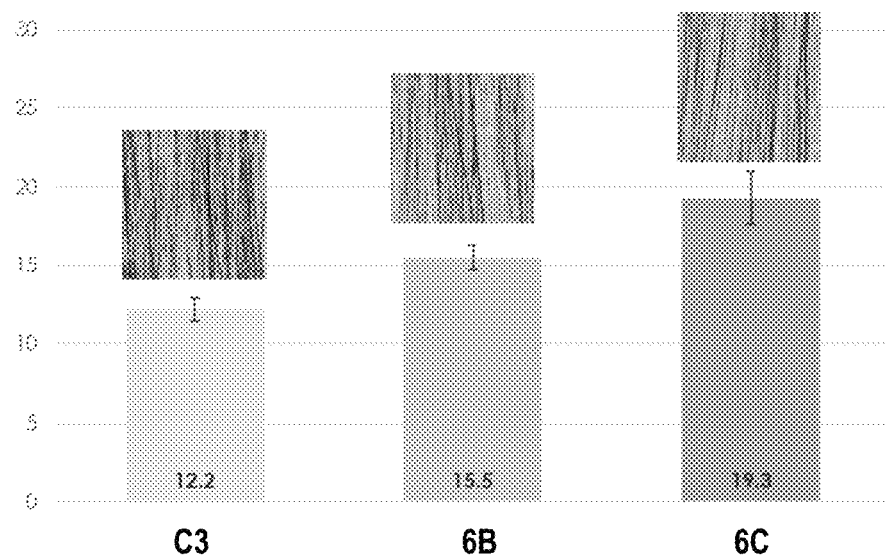

The color change for each swatch was evaluated by determining the ΔE of the color of the hair after treatment compared to the color of the hair before treatment. The ΔE for hair treated with each of systems 6B-6C, and composition C3, is shown in Table 6-2 and FIG. 3B. As can be seen, the ΔE hair treated with system 6B (pre-treatment composition with polyethyleneimine having a molecular weight of 2000) is lower than that of hair treated with system 6C (pre-treatment composition with polyethyleneimine having a molecular weight of 800), but is higher that hair treated with dyeing composition C3 with no pre-treatment.

Example 6-2 shows that systems according to the disclosure comprising pre-treatment compositions having non-surface active amine-based compounds with lower molecular weight surprisingly provide greater change in color compared to systems comprising pre-treatment compositions having amine-based compounds with higher molecular weight.

Figure 3C:
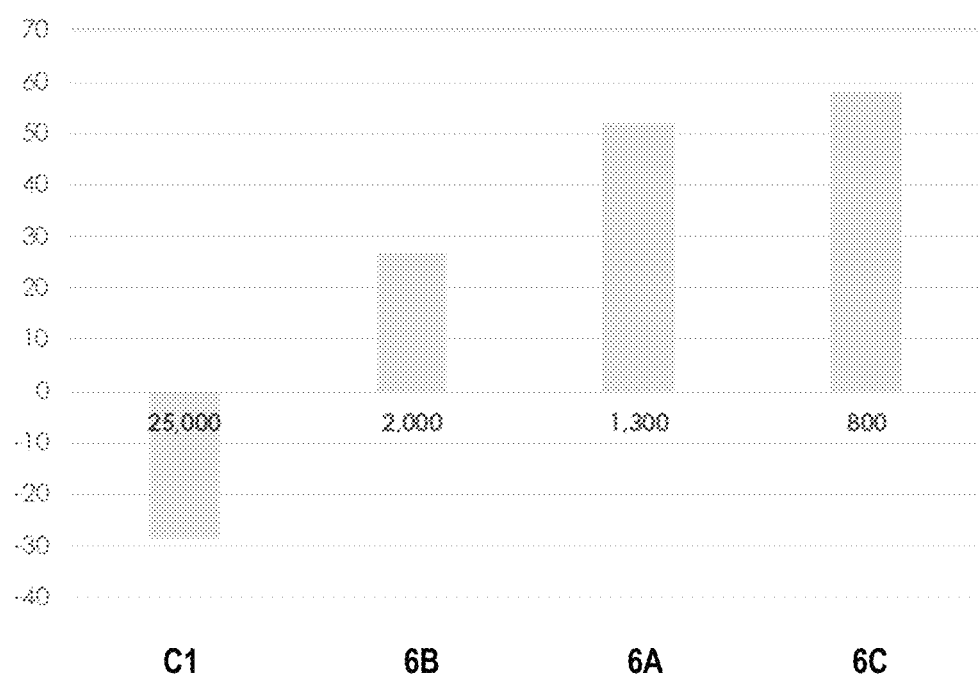
FIG. 3C is a graph showing the percent change in ΔE (y-axis) of hair treated with systems comprising pre-treatment compositions having polyethyleneimine of different molecular weights followed by dyeing compositions comprising microtube-dye composites. This graph demonstrates that, as molecular weight of the non-surface active amine-based compound in systems and methods according to the disclosure decreases, the ΔE surprisingly increases.

As can be seen in FIG. 3C, which shows the percent change in ΔE of hair treated with systems comprising pre-treatment compositions comprising non-surface active amine-based compounds followed by dyeing compositions according to the disclosure, as molecular weight of the non-surface active amine-based compound decreases, the ΔE surprisingly increases. Example 6 therefore demonstrates the surprising and unexpected improvement in color deposition on hair using systems having a pre-treatment step according to the disclosure.

Example 7—Demonstration of Benefit of Amine-Based Pre-Treatment Compounds

The following Examples 7-1 and 7-2 demonstrate the surprising improvement in color deposition on the hair using systems and methods including a pre-treatment composition comprising amine-based compounds. The process for treating hair with systems 7A-7B and C4-05 was the same as described in Example 4-1, and the process for treating hair with compositions C6-C7 was the same as described in Example 4-2.

Example 7-1—Comparison of Color Imparted by Systems Comprising Pre-Treatment Compositions Having Amine-Based Compounds with Color Imparted by Pre-Treatment Compositions not Having Amine-Based Compounds The color imparted to hair by system 7A according to the disclosure comprising a combination of pre-treatment composition 2C of Example 2 and dyeing composition 3F of Example 3 was compared with the color imparted to hair by comparative system C4 comprising a combination of pre-treatment composition AA comprising acetic acid as the pre-treatment agent and dyeing composition 3F of Example 3, as set forth in Table 7-1. The color imparted to hair by comparative composition C6 was also evaluated, without a pre-treatment step.

TABLE 7-1

| System | Pre-treatment composition | Molecular weight of amine | pH pre-treatment | Dyeing composition | pH dyeing | ΔE |
| --- | --- | --- | --- | --- | --- | --- |
| 7A | 2C | 1300 | 3 | 3F | 7 | 27.2 |
| C4 | AA* | 60.05 | 3 | 3F | 7 | 18.2 |
| C6 | — | — | — | 3F | 7 | 18.8 |

*AA is a 1% aqueous solution of acetic acid (molecular weight 60.05) having a pH of 3

Figure 4A:
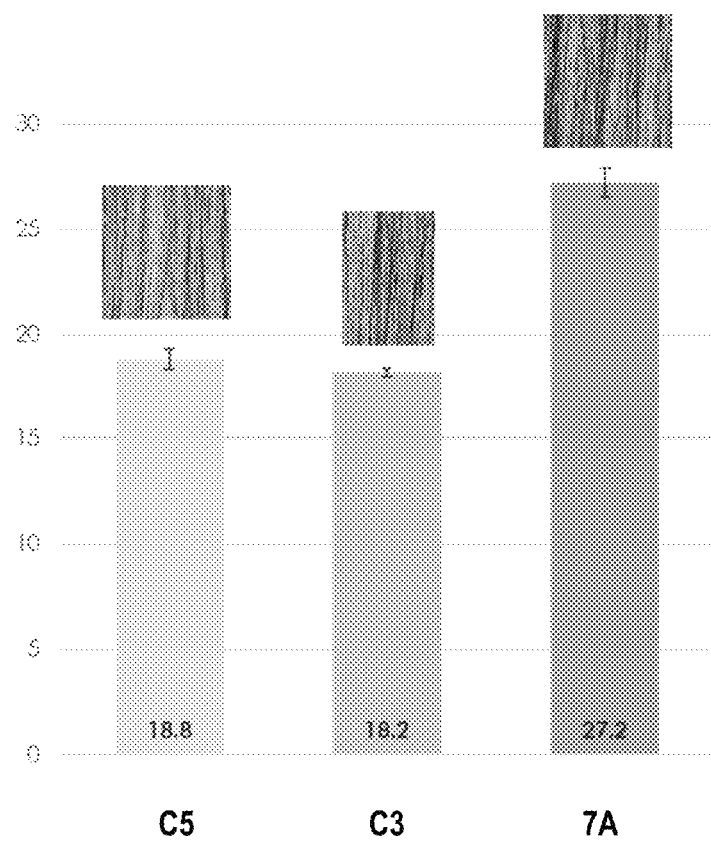

The color change for each swatch was evaluated by determining the ΔE of the color of the hair after treatment compared to the color of the hair before treatment. The ΔE for hair treated with each of systems 7A and C4, and composition C6, is shown in Table 7-1 and FIG. 4A. As can be seen, the ΔE for hair treated with inventive system 7A (pre-treatment composition with amine-based compound having a molecular weight of 1300) is greater than that of either hair treated with comparative system C4 (pre-treatment composition with non-amine-based compound having a molecular weight of 60.05) or with dyeing composition C6 with no pre-treatment. Notably, the ΔE for hair treated with acetic acid as the pre-treatment agent was lower than hair treated with composition C6 with no pre-treatment.

Example 7-1 thus demonstrates that systems according to the disclosure comprising pre-treatment compositions having amine-based compounds surprisingly provide greater change in color compared to systems comprising pre-treatment compositions having non-amine-based compounds, even at the same pH.

Example 7-2—Comparison of Color Imparted by Systems Comprising Pre-Treatment Compositions Having Amine-Based Compounds with Color Imparted by Pre-Treatment Compositions not Having Amine-Based Compounds The color imparted to hair by system 7B according to the disclosure comprising a combination of pre-treatment composition 2C of Example 2 and dyeing composition 3C of Example 3 was compared with color imparted to hair by comparative system C5 comprising a combination of pre-treatment composition TA comprising tannic acid as the pre-treatment agent and dyeing composition 3C of Example 3, as set forth in Table 7-2. The color imparted to hair by comparative composition C7 was also evaluated, without a pre-treatment step.

TABLE 7-2

| System | Pre-treatment composition | Molecular weight of amine | pH pre-treatment | Dyeing composition | pH dyeing | ΔE |
| --- | --- | --- | --- | --- | --- | --- |
| 7B | 2C | 1300 | 3 | 3C | 7 | 16.4 |
| C5 | TA* | 1701.2 | 3 | 3C | 7 | 5.4 |
| C7 | — | — | — | 3C | 7 | 6.8 |

*TA is a 3% aqueous solution of tannic acid (molecular weight 1701.2) having a pH of 3

Figure 4B:
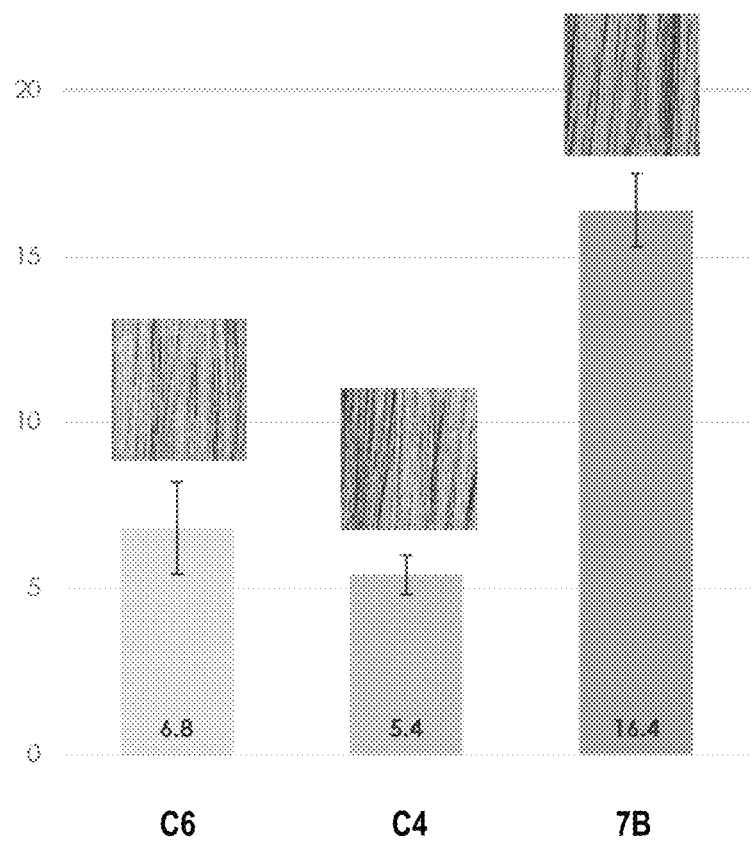

The color change for each swatch was evaluated by determining the ΔE of the color of the hair after treatment compared to the color of the hair before treatment. The ΔE for hair treated with each of systems 7B and C5, and composition C7, is shown in Table 7-2 and FIG. 4B. As can be seen, the ΔE for hair treated with inventive system 7B (pre-treatment composition with amine-based compound having a molecular weight of 1300) is greater than that of either hair treated with comparative system C5 (pre-treatment composition with non-amine-based compound having a molecular weight of 1701.2) or with dyeing composition C7 with no pre-treatment. Notably, the ΔE for hair treated with tannic acid as the pre-treatment agent was lower than hair treated with composition C7 with no pre-treatment.

Example 7-2 shows that systems according to the disclosure comprising pre-treatment compositions having amine-based compounds surprisingly provide greater change in color compared to systems comprising pre-treatment compositions having non-amine-based compounds, even when the pre-treatment agents are of similar molecular weight and the pre-treatment compositions have the same pH.

Example 7 therefore demonstrates the surprising and unexpected improvement in color deposition on hair using systems having a pre-treatment step with a non-surface active amine-based compound according to the disclosure.

The above examples demonstrate that the systems, methods, and kits according to the disclosure surprisingly and unexpectedly provide improved color enhancement to hair relative to those not according to the disclosure.

The invention claimed is:

1. A method of altering the color of hair comprising:
   (a) applying to the hair a pre-treatment composition comprising at least one non-surface active amine-based compound and at least one solvent, and
   (b) applying to the hair a dyeing composition comprising at least one microtube-dye composite and at least one solvent,
      wherein, in the microtube-dye composite, the dye comprises at least one hair dyeing agent.

2. The method according to claim 1, wherein the at least one non-surface active amine-based compound has a molecular weight of less than about 10,000.

3. The method according to claim 1, wherein the at least one non-surface active amine-based compound has at least one nitrogen in the main chain and/or has at least one imine group HN=C.

4. The method according to claim 1, wherein the at least one non-surface active amine-based compound is chosen from synthetic and/or natural polyamines.

5. The method according to claim 1, wherein the pre-treatment composition and/or the dyeing composition has a pH of about 7 or less.

6. The method according to claim 1, wherein the microtube-dye composite comprises a halloysite-dye composite comprising at least one dyeing agent.

7. The method according to claim 1, wherein the pre-treatment composition and the dyeing composition have a pH ranging from about 2 to about 6.

8. The method according to claim 1, comprising a step of drying the hair after the pre-treatment composition is applied to the hair and before the dyeing composition is applied to the hair, wherein the pre-treatment composition is not rinsed from the hair before the hair is dried.

9. The method according to claim 8, wherein the pre-treatment composition is left on the hair for a leave-in period ranging from about 1 minute to about 60 minutes before the hair is dried.

10. The method according to claim 1, wherein steps (a) and/or (b) are repeated one or more times.

11. The method according to claim 1, wherein the pre-treatment composition comprises a total amount of non-surface active amine-based compounds ranging from about 0.001% to about 20% by weight, relative to the total weight of the pre-treatment composition.

12. The method according to claim 1, wherein the dyeing composition comprises a total amount of microtube-dye composites ranging from about 0.01% to about 15% by weight, based on the weight of the dyeing composition.

13. The method according to claim 1, comprising:
   (a) applying to the hair a pre-treatment composition comprising water and at least one non-surface active amine-based compound having a molecular weight of less than about 10,000,
   (b) leaving the pre-treatment composition on the hair for a leave-in period ranging from about 3 minutes to about 40 minutes,
   (c) drying the hair without removing the pre-treatment composition from the hair, and
   (d) applying to the hair a dyeing composition comprising water and at least one microtube-dye composite comprising halloysite,
      wherein in the microtube-dye composite, the dye comprises at least one hair dyeing agent.

14. The method according to claim 13, wherein the pre-treatment composition and/or the dyeing composition has a pH of less than about 7.

15. The method according to claim 13, wherein the pre-treatment composition and the dyeing composition each have a pH ranging from about 2 to about 6, and wherein the at least one non-surface active amine-based compound has a molecular weight ranging from about 50 to about 5000.

16. A system for altering the color of hair comprising:
   (a) a pre-treatment composition comprising at least one non-surface active amine-based compound and at least one solvent, and
   (b) a dyeing composition comprising at least one microtube-dye composite and at least one solvent,
      wherein, in the microtube-dye composite, the dye comprises at least one hair dyeing agent.

17. The system according to claim 16, wherein the at least one non-surface active amine-based compound has a molecular weight of less than about 10,000.

18. The system according to claim 16, wherein the wherein the at least one non-surface active amine-based compound has at least one nitrogen in the main chain and/or has at least one imine group HN=C.

19. The system according to claim 16, wherein the at least one non-surface active amine-based compound is chosen from synthetic and/or natural polyamines.

20. The system according to claim 16, wherein the pre-treatment composition and/or the dyeing composition has a pH of about 7 or less.

21. The system according to claim 16, wherein the microtube-dye composite comprises a halloysite-dye composite comprising at least one hair dyeing agent.

22. The system according to claim 16, wherein the pre-treatment composition and the dyeing composition have a pH ranging from about 2 to about 6.

23. The system according to claim 16, comprising:
   (a) a pre-treatment composition comprising at least one non-surface active amine-based compound having a molecular weight ranging from about 50 to about 5,000, and
   (b) a dyeing composition comprising at least one microtube-dye composite comprising halloysite and at least one solvent,
      wherein the pre-treatment composition and the dyeing composition each have a pH ranging from about 2 to about 6.

24. A kit for altering the color of hair comprising:
   (a) a first container containing a pre-treatment composition comprising at least one non-surface active amine-based compound and optionally at least one solvent, and
   (b) a second container containing a dyeing composition comprising at least one microtube-dye composite and optionally at least one solvent,
      wherein, in the microtube-dye composite, the dye comprises at least one hair dyeing agent.

25. The kit according to claim 24, wherein the non-surface active amine-based compound has a molecular weight ranging from about 100 to about 10,000, and wherein the pre-treatment composition and/or the dyeing composition has a pH of less than or equal to about 7.

* * * * *